United States Patent
Marshall et al.

(10) Patent No.: US 10,137,295 B2
(45) Date of Patent: Nov. 27, 2018

(54) IMPLANTABLE EXTRAVASCULAR ELECTRICAL STIMULATION LEAD HAVING IMPROVED SENSING AND PACING CAPABILITY

(71) Applicant: Medtronic, Inc., Minneapolis, MN (US)

(72) Inventors: Mark T. Marshall, Forest Lake, MN (US); Jian Cao, Shoreview, MN (US); Melissa G. T. Christie, Andover, MN (US); Paul J. DeGroot, Shoreview, MN (US); Vladimir P. Nikolski, Blaine, MN (US); Amy E. Thompson-Nauman, Ham Lake, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 15/860,310

(22) Filed: Jan. 2, 2018

(65) Prior Publication Data
US 2018/0117303 A1     May 3, 2018

Related U.S. Application Data

(63) Continuation of application No. 14/695,255, filed on Apr. 24, 2015, now Pat. No. 9,855,414.
(Continued)

(51) Int. Cl.
*A61N 1/00* (2006.01)
*A61N 1/05* (2006.01)
*A61N 1/39* (2006.01)

(52) U.S. Cl.
CPC ............ *A61N 1/05* (2013.01); *A61N 1/0504* (2013.01); *A61N 1/3918* (2013.01)

(58) Field of Classification Search
CPC .................................................... A61N 1/3962
(Continued)

(56) References Cited

U.S. PATENT DOCUMENTS 3,496,932 A    2/1970  Prisk et al.
4,030,509 A    6/1977  Heilman et al.
(Continued)

FOREIGN PATENT DOCUMENTS

WO       2009006331 A1    1/2009

OTHER PUBLICATIONS

Tung et al., "Initial Experience of Minimal Invasive Extra Cardiac Placement of High Voltage Defibrillator Leads," Canadian Cardiovascular Congress 2007, Oct. 2007, vol. 23, Supplemental SC, Abstract 0697, http://wwww.pulsus.com/ccc2007/abs/0697.htm, 2 page.

(Continued)

*Primary Examiner* — Nadia A Mahmood

(57) ABSTRACT

Implantable medical electrical leads having electrodes arranged such that a defibrillation coil electrode and a pace/sense electrode(s) are concurrently positioned substantially over the ventricle when implanted as described. The leads include an elongated lead body having a distal portion and a proximal end, a connector at the proximal end of the lead body, a defibrillation electrode located along the distal portion of the lead body, wherein the defibrillation electrode includes a first electrode segment and a second electrode segment proximal to the first electrode segment by a distance. The leads may include at least one pace/sense electrode, which in some instances, is located between the first defibrillation electrode segment and the second defibrillation electrode segment.

29 Claims, 9 Drawing Sheets

Related U.S. Application Data

(60) Provisional application No. 61/984,148, filed on Apr. 25, 2014.

(58) Field of Classification Search
USPC .................................................. 607/4, 129
See application file for complete search history.

(56) References Cited

U.S. PATENT DOCUMENTS

| | | |
|---|---|---|
| 4,161,952 A | 7/1979 | Kinney et al. |
| 4,355,646 A | 10/1982 | Kallok et al. |
| 4,628,934 A | 12/1986 | Pohndorf et al. |
| 4,765,341 A | 8/1988 | Mower et al. |
| 4,922,927 A | 5/1990 | Fine et al. |
| 4,947,866 A | 8/1990 | Lessar et al. |
| 4,991,603 A | 2/1991 | Cohen et al. |
| 5,105,826 A | 4/1992 | Smits et al. |
| 5,174,288 A | 12/1992 | Bardy et al. |
| 5,176,135 A | 1/1993 | Fain et al. |
| 5,203,348 A | 4/1993 | Dahl et al. |
| 5,282,845 A | 2/1994 | Bush et al. |
| 5,325,870 A | 7/1994 | Kroll et al. |
| 5,336,253 A | 8/1994 | Gordon et al. |
| 5,342,407 A | 8/1994 | Dahl et al. |
| 5,387,233 A | 2/1995 | Alferness et al. |
| 5,456,706 A | 10/1995 | Pless et al. |
| 5,476,502 A | 12/1995 | Rubin |
| 5,522,874 A | 6/1996 | Gates |
| 5,531,782 A | 7/1996 | Kroll et al. |
| 5,534,022 A | 7/1996 | Hoffman et al. |
| 5,545,205 A | 8/1996 | Schulte et al. |
| 5,654,030 A | 8/1997 | Munshi et al. |
| 5,683,443 A | 11/1997 | Munshi et al. |
| 5,800,465 A | 9/1998 | Thompson et al. |
| 5,810,887 A | 9/1998 | Accorti, Jr. et al. |
| 5,833,714 A | 11/1998 | Loeb |
| 5,849,031 A | 12/1998 | Martinez et al. |
| 5,916,243 A | 6/1999 | KenKnight et al. |
| 5,922,024 A | 7/1999 | Janzen et al. |
| 5,925,073 A | 7/1999 | Chastain et al. |
| 6,066,165 A | 5/2000 | Racz |
| 6,256,541 B1 | 7/2001 | Heil et al. |
| 6,321,123 B1 | 11/2001 | Morris et al. |
| 6,327,498 B1 | 12/2001 | Kroll |
| 6,345,198 B1 | 2/2002 | Mouchawar et al. |
| 6,430,449 B1 | 8/2002 | Hsu et al. |
| 6,658,289 B2 | 12/2003 | Helland |
| 6,721,597 B1 | 4/2004 | Bardy et al. |
| 6,721,598 B1 | 4/2004 | Helland et al. |
| 7,047,086 B2 | 5/2006 | Taskiran et al. |
| 7,313,444 B2 | 12/2007 | Pianca et al. |
| 7,465,341 B2 | 12/2008 | Eliasson |
| 7,668,601 B2 | 2/2010 | Hegland et al. |
| 7,684,864 B2 | 3/2010 | Olson et al. |
| 7,761,150 B2 | 7/2010 | Ghanem et al. |
| 7,899,555 B2 | 3/2011 | Morgan et al. |
| 7,917,216 B1 | 3/2011 | Ryu et al. |
| 8,017,179 B2 | 9/2011 | Atanasoka et al. |
| 8,498,721 B2 | 7/2013 | Scheiner et al. |
| 9,855,414 B2 | 1/2018 | Marshall et al. |
| 2002/0103523 A1 | 8/2002 | Helland et al. |
| 2003/0105501 A1 | 6/2003 | Warman et al. |
| 2005/0209646 A1 | 9/2005 | Wanasek |
| 2005/0277990 A1 | 12/2005 | Ostroff et al. |
| 2006/0020316 A1 | 1/2006 | Martinez et al. |
| 2006/0041295 A1 | 2/2006 | Osypka |
| 2006/0247753 A1 | 11/2006 | Wenger et al. |
| 2007/0250142 A1 | 10/2007 | Francis et al. |
| 2008/0046059 A1 | 2/2008 | Zarembo et al. |
| 2008/0195163 A1 | 8/2008 | Scharmer |
| 2009/0248117 A1 | 10/2009 | Nippoldt et al. |
| 2009/0264780 A1 | 10/2009 | Schilling |
| 2009/0287266 A1 | 11/2009 | Zdeblick |
| 2010/0114195 A1 | 5/2010 | Bumes et al. |
| 2010/0121421 A1 | 5/2010 | Duncan et al. |
| 2010/0198284 A1 | 8/2010 | Zhou et al. |
| 2010/0305675 A1 | 12/2010 | Laske et al. |
| 2012/0029335 A1 | 2/2012 | Sudam et al. |
| 2013/0023944 A1 | 1/2013 | Doerr |
| 2013/0338730 A1 | 12/2013 | Shiroff et al. |
| 2014/0052120 A1 | 2/2014 | Benscoter et al. |
| 2015/0306375 A1 | 10/2015 | Marshall et al. |
| 2015/0306410 A1 | 10/2015 | Marshall et al. |

OTHER PUBLICATIONS

D'Callaghan et al., "Current Status of Implantable Cardioverter-Defibrillators," Current Problems in Cardiology, vol. 22, No. 12, Dec. 1997, 66 pages.

International Search Report and the Written Opinion from International Application No. PCT/US2015/064606, dated Apr. 25, 2016, 11 pp.

International Search Report and the Written Opinion from International Application No. PCT/US2015/027478, dated Jul. 10, 2015, 9 pp.

International Preliminary Report on Patentability from International Application No. PCT/US2015/027478, dated Oct. 25, 2016, 6 pp.

Guenther et al., "Substernal Lead Implantation: A Novel Option to Manage DFT Failure in S-ICD patients," Clinical Research Cardiology, Published On-line Oct. 2, 2014, 3 pages.

Ganapathy et al., "Implantable Device to Monitor Cardiac Activity with Sternal Wires," Pace, vol. 37, Dec. 2014, 11 pages.

Prosecution History from U.S. Appl. No. 14/519,436, filed Feb. 11, 2016 through Oct. 23, 2017, 79 pp.

Prosecution History from U.S. Appl. No. 14/695,255, filed Jan. 5, 2016 through Aug. 25, 2017, 91 pp.

Communication pursuant to Rules 161 (1) and 162 EPC from counterpart European Patent Application No. 15721469.3, dated Dec. 16, 2016, 2 pp.

Preliminary Amendments to counterpart European Patent Application No. 15721469.3, filed on Nov. 24, 2016, 6 pp.

IMPLANTABLE EXTRAVASCULAR ELECTRICAL STIMULATION LEAD HAVING IMPROVED SENSING AND PACING CAPABILITY

This application is a continuation of U.S. patent application Ser. No. 14/695,255 filed Apr. 24, 2015, which claims the benefit of U.S. Provisional Application No. 61/984,148 filed on Apr. 25, 2014, the entire content of both of which are incorporated herein by reference in their entirety.

FIELD OF THE INVENTION

The present application relates to electrical stimulation leads and, more particularly, electrical stimulation leads with improved sensing and/or pacing capability for use in extravascular applications.

BACKGROUND OF THE INVENTION

Malignant tachyarrhythmia, for example, ventricular fibrillation (VF), is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients at high risk of ventricular fibrillation, the use of an implantable cardioverter-defibrillator (ICD) system has been shown to be beneficial at preventing SCD. An ICD system includes an ICD, which is a battery powered electrical stimulation device, that may include an electrical housing electrode (sometimes referred to as a can electrode), that is coupled to one or more electrical stimulation leads. The electrical stimulation leads may be placed within the heart, within vasculature near the heart (e.g., within the coronary sinus), attached to the outside surface of the heart (e.g., in the pericardium or epicardium), or implanted subcutaneously above the ribcage/sternum. If an arrhythmia is detected, the ICD may generate and deliver a pulse (e.g., cardioversion or defibrillation shock) via the electrical stimulation leads to shock the heart and restore its normal rhythm.

SUMMARY

Extravascular and/or extracardiac implanted electrical stimulation leads, e.g., subcutaneously implanted electrical stimulation leads or substernally implanted electrical stimulation leads reside in a plane of tissue or muscle between the skin and sternum for subcutaneous, or reside in a plane of tissue or muscle between the sternum and the heart for substernal. Due to the distance between the heart and electrodes of the electrical stimulation leads, to achieve improved pacing, sensing, and/or defibrillation, the pace/sense electrodes and the defibrillation coil electrode should be positioned in the plane of tissue such that the electrodes are located directly above or proximate the surface of the cardiac silhouette, most typically the ventricular surface. For example, the electrode(s) used to deliver pacing pulses should be positioned in a vector substantially over (and in some instances centered over) the chamber to be paced to produce the lowest pacing capture thresholds for pacing. Likewise, the electrode(s) used to sense cardiac electrical activity of the heart should be positioned substantially over (and in some instances centered over) the chamber to be sensed to obtain the best sensed signal. For shocking purposes, it is preferred to have the defibrillation coil electrode positioned substantially over (and in some instances centered over) the center of the chamber to be shocked.

Current medical electrical lead designs used for subcutaneous defibrillation include a single defibrillation coil electrode located between a first pace/sense electrode distal to the defibrillation coil and a second pace/sense electrode proximal to the defibrillation coil. In such a configuration, it is not possible to concurrently position both the defibrillation coil electrode and the pace/sense electrode(s) substantially over the center of the ventricle. Electrical stimulation leads described herein are designed such that concurrent positioning of the defibrillation electrode and the pace/sense electrode(s) is possible.

In one example, this disclosure is directed to an implantable medical electrical lead comprising an elongated lead body having a distal portion and a proximal end, a connector at the proximal end of the lead body, and a defibrillation electrode located along the distal portion of the lead body. The defibrillation electrode includes a first electrode segment and a second electrode segment. The second electrode segment is spaced proximal to the first electrode segment by a distance. The lead also includes at least one pace/sense electrode located between the first segment and the second segment of the defibrillation electrode.

In another example, this disclosure is directed to an implantable medical electrical lead an elongated lead body having a distal portion and a proximal end, a connector at the proximal end of the lead body, and a defibrillation electrode located along the distal portion of the lead body. The defibrillation electrode includes a first electrode segment and a second electrode segment spaced proximal to the first electrode segment by approximately 1-3 centimeters (cm). The lead also includes at least one pace/sense electrode located between the first electrode segment and the second electrode segment of the defibrillation electrode.

In a further example, this disclosure is directed to an extravascular implantable cardioverter-defibrillator system comprising an implantable cardioverter-device (ICD) that includes a therapy module configured to generate and deliver electrical stimulation therapy and an extravascular implantable medical electrical lead electrically coupled to the therapy module. The lead includes an elongated lead body having a distal portion and a proximal end, a connector at the proximal end of the lead body, and a defibrillation electrode located along the distal portion of the lead body. The defibrillation electrode includes a first electrode segment and a second electrode segment spaced proximal to the first electrode segment by a distance. The lead also includes at least one pace/sense electrode located between the first electrode segment and the second electrode segment of the defibrillation electrode.

In a further example, this disclosure is directed to an extravascular implantable cardioverter-defibrillator (ICD) system comprising an extravascular implantable medical electrical lead and an ICD coupled to the extravascular lead. The extravascular lead includes an elongated lead body having a distal portion and a proximal end, a connector at the proximal end of the lead body, and a plurality of defibrillation electrode segments located along the distal portion of the lead body. The plurality of defibrillation electrode segments include at least a first defibrillation electrode segment and a second defibrillation electrode segment spaced proximal to the first defibrillation electrode segment by a distance. The extravascular lead further includes a first pace/sense electrode located distal to the first defibrillation electrode segment and a second pace/sense electrode located proximal to the second defibrillation electrode segment. The extravascular lead further includes a plurality of conductors extending within the elongated body from the connector to the distal portion, wherein each of the first defibrillation electrode segment, the second defibrillation electrode segment, the first pace/sense electrode, and the second pace/sense electrode are coupled to a different one of the plurality of conductors within the lead body. The ICD includes a therapy module configured to generate and deliver electrical stimulation therapy and a switch module configured to selectively couple the therapy module to an electrode vector in which both the first and second defibrillation electrode segments simultaneously function as a cathode for delivery of defibrillation therapy.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1A:
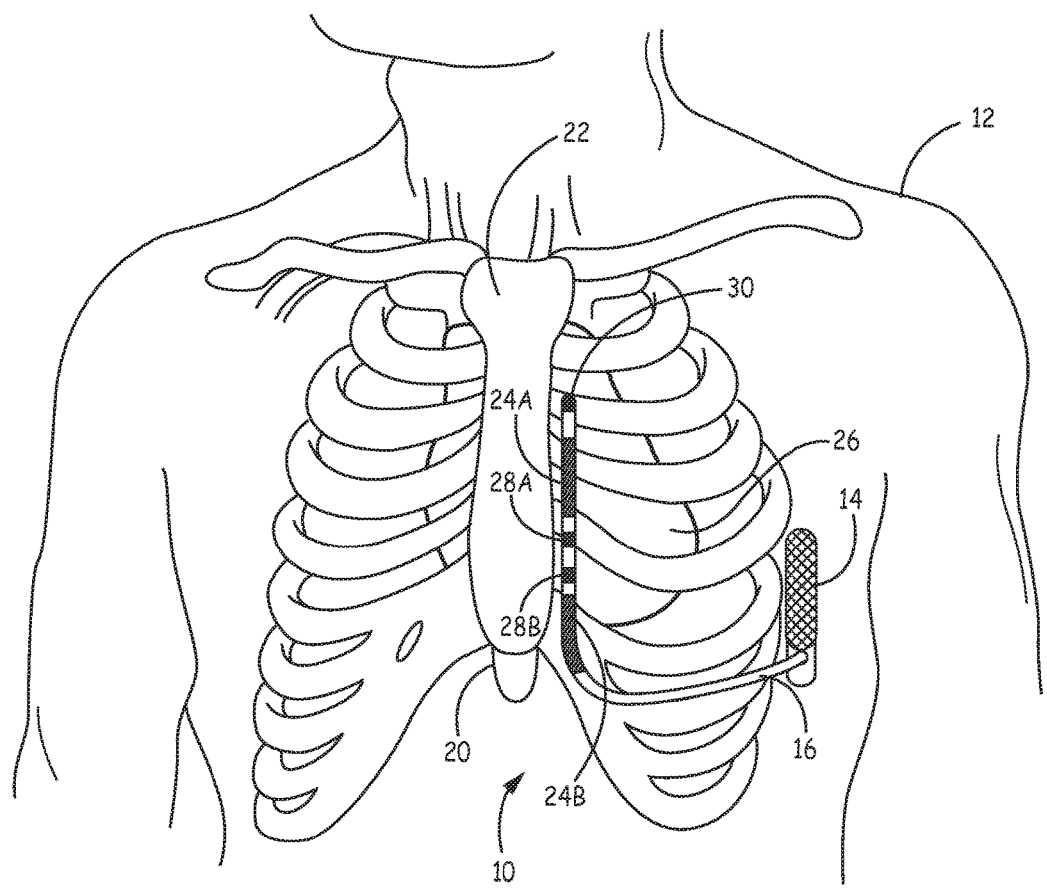
FIGS. 1A and 1B are conceptual drawings illustrating various views of a patient implanted with an example extravascular implantable cardioverter-defibrillator (ICD) system.
Figure 1B:
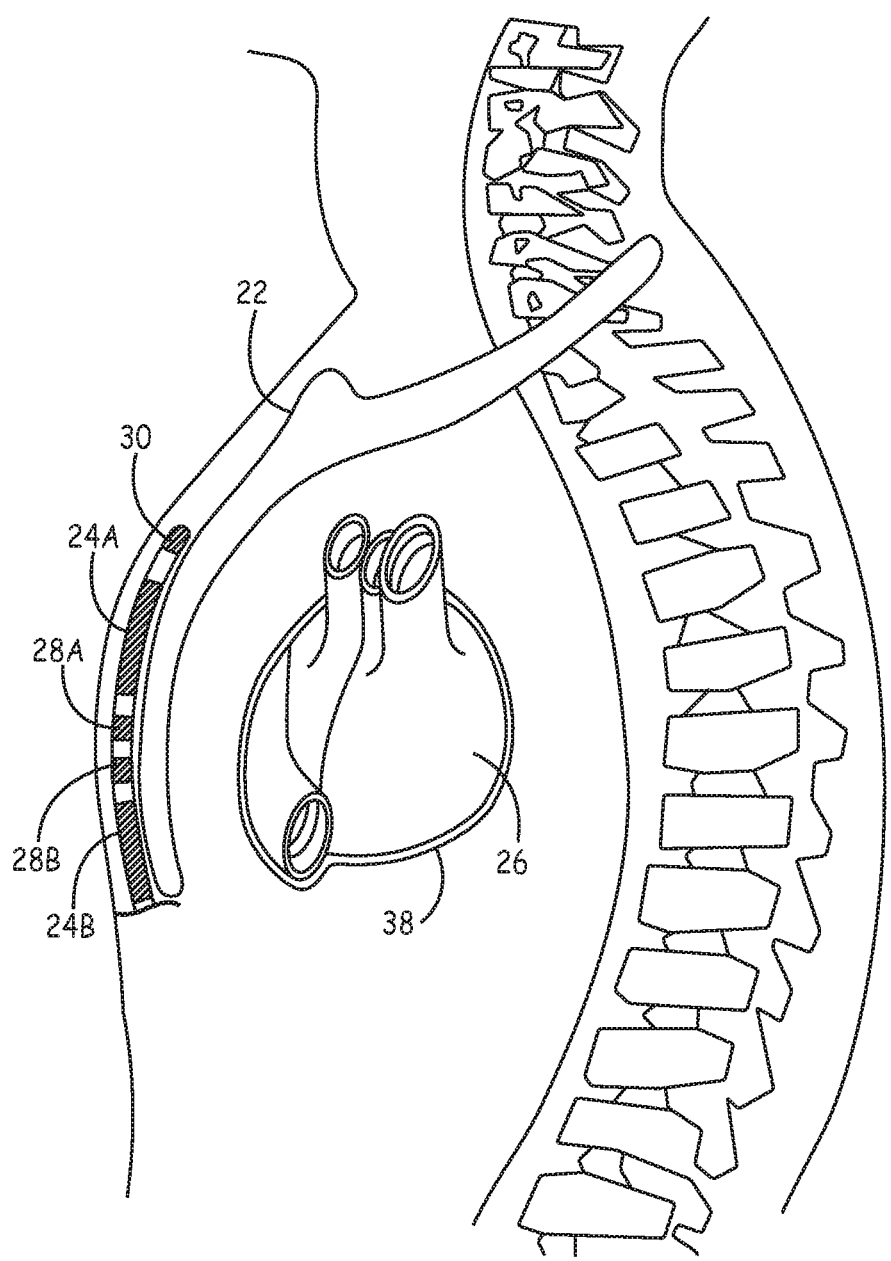

FIGS. 1A and 1B are conceptual diagrams of an extravascular and/or extracardiac implantable cardioverter-defibrillator (ICD) system 10. ICD system 10 is subcutaneously implanted within a patient 12. FIG. 1A is a front view of ICD system 10 implanted within patient 12. FIG. 1B is a side view of ICD system 10 implanted within patient 12. ICD system 10 includes an ICD 14 connected to an extravascular and/or extracardiac electrical stimulation lead 16. FIGS. 1A and 1B are described in the context of an ICD system capable of providing defibrillation and/or cardioversion shocks and, in some instances, pacing pulses. However, the techniques of this disclosure may also be used in the context of other implantable medical devices configured to provide electrical stimulation pulses to stimulate other portions of the body of patient 12.

ICD 14 may include a housing that forms a hermetic seal that protects components of ICD 14. The housing of ICD 14 may be formed of a conductive material, such as titanium or titanium alloy. The housing of ICD 14 may function as a housing electrode (sometimes referred to as a can electrode). In other instances, the housing of ICD 14 may include a plurality of electrodes on an outer portion of the housing. The can electrode and/or the plurality of electrodes on the outer portion of the housing may be coated with a material, such as titanium nitride. ICD 14 may also include a connector assembly (also referred to as a connector block or header) that includes electrical feedthroughs through which electrical connections are made between conductors extending within the body of lead 16 and electronic components included within the housing of ICD 14. As will be described in further detail herein, housing may house one or more processors, memories, transmitters, receivers, sensors, sensing circuitry, therapy circuitry, power sources and other appropriate components. The housing is configured to be implanted in a patient, such as patient 12. ICD 14 is implanted subcutaneously on the left side of patient 12 above the ribcage. ICD 14 may, in some instances, be implanted between the left posterior axillary line and the left anterior axillary line of patient 12. ICD 14 may, however, be implanted at other subcutaneous locations on patient 12 as described later.

Lead 16 includes an elongated lead body having a proximal end that includes a connector (not shown) configured to be connected to ICD 14 and a distal portion that includes one or more electrodes. In the example illustrated in FIGS. 1A and 1B, the distal portion of lead 16 includes defibrillation electrode segments 24A and 24B, and pace/sense electrodes 28A, 28B, and 30. In some cases, defibrillation electrode segments 24A and 24B may together form a defibrillation electrode in that they are configured to be activated concurrently. Alternatively, defibrillation electrode segments 24A and 24B may form separate defibrillation electrodes in which case each of the electrodes 24A and 24B may be activated independently. In some instances, ICD 14 may include switching mechanisms to allow defibrillation electrode segments 24A and 24B coupled to separate conductors to be utilized as a single defibrillation electrode (e.g., activated concurrently to form a common cathode or anode) or as separate defibrillation electrodes, (e.g., activated individually). Electrode segments 24A and 24B are referred to as defibrillation electrode segments or defibrillation electrodes because they are utilized, individually or collectively, for delivering high voltage stimulation therapy (e.g., cardioversion or defibrillation shocks). However, electrode segments 24A and 24B may also be utilized to provide pacing functionality, sensing functionality or both pacing and sensing functionality in addition to or instead of high voltage stimulation therapy. In this sense, the use of the terms "defibrillation electrode segments" or "defibrillation electrode" should not be considered as limiting the electrode segments to use in only high voltage applications.

Lead 16 extends subcutaneously or submuscularly above the ribcage from the connector block of ICD 14 toward a center of the torso of patient 12, e.g., toward xiphoid process 20 of patient 12. At a location near xiphoid process 20, lead 16 bends or turns and extends superior subcutaneously above the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled lateral from sternum 22 at either the proximal or distal end, or the like. Alternatively, lead 16 may be placed along other subcutaneous paths. The path of lead 16 may depend on the location of ICD 14 or other factors.

The elongated lead body of lead 16 contains a plurality of electrical conductors (not illustrated) that extend within the lead body from the connector at the proximal lead end to defibrillation electrode segments 24A and 24B and pace/sense electrodes 28A, 28B, and 30 located along the distal portion of the lead body of lead 16. The elongated lead body may have a generally uniform shape along the length of the lead body. In one example, the elongated lead body may have a generally tubular or cylindrical shape along the length of the lead body. The elongated lead body may have a diameter of between 3 and 9 French (Fr) in some instances. However, lead bodies of less than 3 Fr and more than 9 Fr may also be utilized. In another example, the distal portion (or all of) the elongated lead body may have a flat, ribbon or paddle shape. In this instance, the width across the flat portion of the flat, ribbon or paddle shape may be between 1 and 3.5 mm. Other lead body designs may be used without departing from the scope of this disclosure. The lead body of lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead body of lead 16 may engage with respective defibrillation electrode segments 24A and 24B and pace/sense electrodes 28A, 28B, and 30. In one example, each of electrodes 28A, 28B, and 30 are electrically coupled to a separate respective conductor within the lead body. Defibrillation electrode segments 24A and 24B may be electrically coupled to a common conductor or to separate conductors.

In one example, defibrillation electrode segments 24A and 24B may be electrically coupled to the same conductor. For example, a single wire conductor (not shown) may be disposed within a lumen of the lead body that is electrically coupled to the connector at the proximal end of the lead body. The single conductor may branch off in the lead body at a predetermined longitudinal position into two or more wire conductors to connect to each of the electrode segments 24A and 24B, respectively. Alternatively, a first conductor may connect to electrode segment 24B and a second conductor may electrically connect defibrillation electrode segment 24B to defibrillation electrode segment 24A such that application of a voltage/current to the first conductor applies the voltage to both defibrillation electrode segment 24A and 24B. In this manner, defibrillation electrode segments 24A and 24B are electrically coupled such that they simultaneously function as a common anode or cathode of an electrode vector.

In other configurations, the defibrillation electrode segments 24A and 24B may be coupled to separate conductors within the lead body 12. For example, a first electrical conductor disposed within the elongate lead body may have a distal end coupled to defibrillation electrode segment 24A and a proximal end coupled to the connector of lead 16 and a second electrical conductor disposed within the elongate lead body has a distal end coupled to the second defibrillation electrode segment 24B and a proximal end coupled to the connector. In this case, each of the defibrillation electrode segments 24A or 24B may be independently utilized as part of an electrode vector. Additionally, ICD 14 may include a switch module that may enable the conductors of both defibrillation electrode segments to be jumpered, tied or otherwise electrically connected (e.g., within the connector block and/or within IMD 14 and/or via an external source of stimulation) such that defibrillation electrode segments 24A and 24B may be electrically coupled together to be simultaneously used as a common anode or cathode of an electrode vector for delivery of electrical stimulation therapy to patient 12 and/or for sensing the electrical signals of the heart of the patient 12.

In any case, the respective conductors may electrically couple to circuitry, such as a therapy module or a sensing module, of ICD 14 via connections in the connector assembly, including associated feedthroughs. The electrical conductors transmit therapy from a therapy module within ICD 14 to one or more of defibrillation electrode segments 24A and 24B and/or pace/sense electrodes 28A, 28B, and 30 and transmit sensed electrical signals from one or more of defibrillation electrode segments 24A and 24B and/or pace/sense electrodes 28A, 28B, and 30 to the sensing module within ICD 14.

Defibrillation electrode segments 24 are located along the distal portion of defibrillation lead 16, e.g., toward the portion of defibrillation lead 16 extending superior near sternum 22. As indicated above, a defibrillation electrode may be formed of a first electrode segment 24A and a second electrode segment 24B proximal to electrode segment 24A. Electrode segments 24A and 24B are separated by a distance. In one example, the first defibrillation electrode segment 24A may be spaced apart from the second defibrillation electrode segment 24B by approximately 1 mm-3 cm. In another example, the first defibrillation electrode segment 24A may be spaced apart from the second defibrillation electrode segment 24B by approximately 0.5-2 cm. In a further example, the first defibrillation electrode segment 24A may be spaced apart from the second defibrillation electrode segment 24B by approximately 0.5-1 cm. In one example, first segment 24A and second segment 24B are each approximately 2-5 cm in length and the proximal end of segment 24A is separated by approximately 1-3 cm from the distal end of segment 24B.

Defibrillation electrode segments 24 may, in one example, be coil electrode segments disposed in-line with, around the exterior of or within the wall of the lead body of lead 16. In other embodiments, however, defibrillation electrode segments 24 may be a flat ribbon electrode, paddle electrode, braided or woven electrode, mesh electrode, directional electrode, patch electrode or other type of electrode that is segmented in the manner described herein. Moreover, in other examples, lead 16 may include more than two defibrillation electrode segments. Further, the two or more defibrillation electrode segments 24 may be of the same or different sizes, shapes, types or materials.

Each of first defibrillation electrode segment 24A and second defibrillation electrode segment 24B may be approximately 1-10 cm in length and, more preferably, 2-6 cm in length and, even more preferably, 3-5 cm in length. However, lengths of greater than 10 cm and less than 1 cm may be utilized without departing from the scope of this disclosure. A total length of defibrillation electrode segments 24 may vary depending on a number of variables. The defibrillation electrode may, in one example, have a total length (e.g., length of the two segments 24A and 24B combined) of between approximately 5-10 centimeters (cm). However, the defibrillation electrode segments 24 may have a total length less than 5 cm and greater than 10 cm in other embodiments. In another example, defibrillation electrode segments 24 may have a total length of approximately 2-16 cm. In some instances, defibrillation segments 24A and 24B may be approximately the same length. In other instances, one of defibrillation segments 24A and 24B may be longer or shorter than the other one of the defibrillation segments 24A and 24B.

Defibrillation lead 16 also includes pace/sense electrodes 28A, 28B, and 30 located along the distal portion of defibrillation lead 16. In the example illustrated in FIGS. 1A and 1B, electrodes 28A and 28B are located between defibrillation electrode segments 24A and 24B and electrode 30 is located distal to defibrillation electrode segment 24A. Electrodes 28A, 28B and 30 are referred to as pace/sense electrodes because they are generally configured for use in low voltage applications, e.g., used as either a cathode or anode for delivery of pacing pulses and/or sensing of cardiac electrical signals. In some instances, electrodes 28A, 28B, and 30 may provide only pacing functionality, only sensing functionality or both and, in some instances, may even be used as part of an electrode vector for high voltage therapy, e.g., defibrillation or cardioversion shocks.

In the example of FIGS. 1A and 1B, electrodes 28A and 28B are illustrated as ring electrodes and electrode 30 is illustrated as a hemispherical tip electrode. However, electrodes 28A, 28B, and 30 may comprise any of a number of different types of electrodes, including ring electrodes, short coil electrodes, paddle electrodes, hemispherical electrodes, directional electrodes, segmented electrodes, or the like, and may be positioned at any position along the distal portion of lead 16. Further, electrodes 28A, 28B, and 30 may be of similar type, shape, size and material or may differ from each other. In another embodiment, for example, electrode 30 may not be a hemispherical tip electrode but instead may be located proximal to the distal end of the lead body of lead 16 and distal defibrillation electrode segment 24A. As another example, electrodes 28A and 28B may be formed of a conductive material that only extends around a portion of the circumference of the lead body, e.g., a half-ring electrode, quarter-ring electrode, or other partial-ring electrode. In another example, electrodes 28A and 28B may be formed of conductive material that extends around the entire circumference of the lead body, but may be partially coated with an insulating material to form the half-ring electrode, quarter-ring electrode, or other partial-ring electrode. Likewise, electrode 30 may be formed into a partial-hemispherical electrode in a similar manner as described above with respect to ring electrodes 28A and 28B. In still other instances, one or more of electrodes 28A, 28B, and 30 may be segmented electrodes (e.g., half- or quarter-ring or hemispherical electrodes) with separate conductors connected to each of the segments or a single conductor with a multiplexor or other switch to switch between the segmented electrodes such that the segments may be used as individual electrodes.

Electrodes 28A, 28B, and 30 of lead 16 may have substantially the same outer diameter as the lead body. In one example, electrodes 28A, 28B, and 30 may have surface areas between 1.6-150 mm$^2$. Electrodes 28A, 28B, and 30 may, in some instances, have substantially the same surface area or different surface areas.

Electrodes 28A, 28B, and 30 may be spaced apart from the respective defibrillation electrode segments 24A and 24B by a distance greater than or equal to 2 mm. In some instances, the distance between the closest electrode segment 24A and 24B and electrodes 28A, 28B, and 30 is greater than or equal to 2 mm and less than or equal to 1.5 cm. In another example, electrodes 28A, 28B, and 30 may be spaced apart from the closest one of electrode segments 24A and 24B by greater than or equal to 5 mm and less than or equal to 1 cm. In a further example, electrodes 28A, 28B, and 30 may be spaced apart from the closest one of electrode segments 24A and 24B by greater than or equal to 6 mm and less than or equal to 8 mm. In another example, electrode 30 (or 28A and 28B) is spaced apart from the distal end of defibrillation electrode segment 24A by a distance, which is less than or equal to 2 cm. The spacing between each of electrodes 28A, 28B, and 30 and the closest one of electrode segments 24A and 24B may be substantially the same or different. However, electrodes 28A, 28B, and 30 may be spaced apart from the distal or proximal end(s) of defibrillation electrode segment 24A or 24B by other distances without departing from the scope of this disclosure.

In some instances, the distal portion of lead 16 from the distal end of lead 16 to the proximal side of the most proximal electrode (e.g., electrode segment 24B in the example of FIGS. 1A and 1B) may be less than or equal 15 cm and, more preferably, less than or equal to 13 cm and even more preferably less than or equal to 10 cm.

Electrodes 28A and 28B are spaced apart from one another along the length of lead 16. The spacing between electrodes 28A and 28B may be dependent upon the configuration of lead 16. For example, the spacing between electrodes 28A and 28B is dependent upon the distance between defibrillation electrode segments 24A and 24B. In one example, electrodes 28A and 28B are spaced apart by less than 2 cm. In some instances, electrodes 28A and 28B may be spaced apart by less than 1 cm. In further instances, electrodes 28A and 28B may be spaced apart from one another by more than 2 cm.

The example configuration of electrodes and dimensions provided above are exemplary in nature and should not be considered limiting of the embodiments described herein. In other embodiments, lead 16 may include less than three pace/sense electrodes or more than three pace/sense electrodes. In further instances, the pace/sense electrodes 28A, 28B, and 30 may be located elsewhere along the length of lead 16, e.g., distal to defibrillation electrode segment 24A, proximal to defibrillation electrode segment 24B, and/or between segments 24A and 24B. For example, lead 16 may include a single pace/sense electrode 28 between defibrillation electrode segments 24A and 24B and no pace/sense electrode distal of defibrillation electrode segment 24A or proximal defibrillation electrode segments 24B. In other examples, lead 16 may include only a single pace/sense electrode 28 between defibrillation electrode segments 24A and 24B and include another discrete electrode(s) distal to defibrillation electrode segment 24A and/or proximal to defibrillation electrode segments 24B. In still other instances, there may be no discrete pace/sense electrodes, in which case the defibrillation electrode segments 24A and 24B would be utilized for pacing and/or sensing. In other examples, lead 16 may include more than two defibrillation electrode segments 24, such as three segments with electrode 28B located between the proximal segment and middle segment and electrode 28A located between the middle segment and the distal segment. Any of these multiple defibrillation electrode segments may be on a single conductor (i.e., all segments electrically coupled to a single conductor extending within the lead body to the connector), individual conductors (i.e., each of the defibrillation electrode segments is electrically coupled to separate conductors extending within the lead body to the connector), or combinations thereof (some segments coupled together to a common conductor and others to individual conductors). Moreover, lead 16 may include any number of pace/sense electrodes proximal to, distal to, or between any of the multiple defibrillation electrode segments.

To achieve improved sensing and/or pacing, it is desirable to have the pace/sense electrodes located substantially over the chamber of heart 26 that is being paced and/or sensed.

For example, it is desirable to locate the pace/sense electrodes over a cardiac silhouette of the ventricle as observed via an anterior-posterior (AP) fluoroscopic view of heart 26 for sensing and/or pacing the ventricle. Likewise, to achieve improved defibrillation therapy, it is desirable to have the defibrillation electrode segments located substantially over the chamber of heart 26 to which the defibrillation or cardioversion shock is being applied, e.g., over a cardiac silhouette of the ventricle as observed via an AP fluoroscopic view of heart 26. In conventional subcutaneous lead designs, it is only possible to position either the defibrillation electrode or the sense electrode over the relevant chamber, but not both.

Leads designed in accordance with any of the techniques described herein can be implanted to achieve desirable electrode positioning for both defibrillation and pacing/sensing. In particular, lead 16 may be implanted such that electrodes 28A and 28B are substantially located over a cardiac silhouette of the ventricle as observed via an AP fluoroscopic view of heart 26. In other words, lead 16 may be implanted such that one or both of a unipolar pacing/sensing vector from electrode 28A and 28B to a housing electrode of ICD 14 are substantially across the ventricle(s) of heart 26. The therapy vector may be viewed as a line that extends from a point on electrode 28A and 28B, e.g., center of electrode 28A and 28B, to a point on the housing electrode of ICD 14, e.g., center of the housing electrode. In another example, the spacing between electrodes 28A and 28B as well as the placement of lead 16 may be such that a bipolar pacing vector between electrode 28A and electrode 28B is centered or otherwise located substantially over the ventricle.

Electrode 30 may be located over the cardiac silhouette of the atrium or near the top of the cardiac silhouette of the atrium or ventricle as observed via an AP fluoroscopic view. As such, electrode 30 may offer an alternate sensing vector and/or provide atrial pacing if needed or desired. Thus, in some instances, lead 16 may be utilized for dual chamber pacing.

Not only are electrodes 28A and 28B located over the ventricle, but defibrillation electrode segments 24A and 24B are substantially over (e.g., centered or otherwise) the cardiac silhouette of the ventricle as observed via an AP fluoroscopic view of heart 26. As such, the therapy vector from defibrillation electrode segments 24A and 24B to the housing of ICD 14 is substantially across the ventricles of heart 26.

In some instances, electrode segments 24 and/or electrodes 28A, 28B, and/or 30 of lead 16 may be shaped, oriented, designed or otherwise configured to reduce extra-cardiac stimulation. For example, electrode segments 24 and/or electrodes 28A, 28B, and/or 30 of lead 16 may be shaped, oriented, designed, partially insulated or otherwise configured to focus, direct or point electrode segments 24 and/or electrodes 28A, 28B, and/or 30 toward heart 26. In this manner, pacing pulses delivered via lead 16 are directed toward heart 26 and not outward toward skeletal muscle. For example, electrode segments 24 and/or electrodes 28A, 28B, and/or 30 of lead 16 may be partially coated or masked with a polymer (e.g., polyurethane) or another coating material (e.g., tantalum pentoxide) on one side or in different regions so as to direct the pacing signal toward heart 26 and not outward toward skeletal muscle. In the case of a ring electrode, for example, the ring electrode may be partially coated with the polymer or other material to form a half-ring electrode, quarter-ring electrode, or other partial-ring electrode.

ICD 14 may obtain sensed electrical signals corresponding with electrical activity of heart 26 via a combination of sensing vectors that include individual electrodes or combinations of electrodes 28A, 28B, and 30 and the housing electrode of ICD 14. For example, ICD 14 may obtain electrical signals sensed using a sensing vector between combinations of electrodes 28A, 28B, and 30 with one another or obtain electrical signals sensed using a sensing vector between any one or more of electrodes 28A, 28B, and 30 and the conductive housing electrode of ICD 14. In some instances, ICD 14 may even obtain sensed electrical signals using a sensing vector that includes one or both defibrillation electrode segments 24A or 24B such as between each other or in combination with one or more of electrodes 28A, 28B, and 30, and/or the housing electrode of ICD 14.

ICD 14 analyzes the sensed electrical signals obtained from one or more of the sensing vectors of lead 16 to monitor for tachyarrhythmia, such as ventricular tachycardia (VT) or ventricular fibrillation (VF). ICD 14 may analyze the heart rate and/or morphology of the sensed electrical signals to monitor for tachyarrhythmia in accordance with any of a number of techniques known in the art. One example technique for detecting tachyarrhythmia is described in U.S. Pat. No. 7,761,150 to Ghanem et al., entitled "METHOD AND APPARATUS FOR DETECTING ARRHYTHMIAS IN A MEDICAL DEVICE." The entire content of the tachyarrhythmia detection algorithm described in Ghanem et al. are incorporated by reference herein in its entirety.

ICD 14 generates and delivers electrical stimulation therapy in response to detecting tachycardia (e.g., VT or VF). In response to detecting the tachycardia, ICD 14 may deliver one or more cardioversion or defibrillation shocks via defibrillation electrode segments 24 of lead 16. ICD 14 may deliver the cardioversion or defibrillation shocks using either, some or all of the electrode segments 24 individually or together as a cathode (or anode) and with the housing electrode as an anode (or cathode). ICD 14 may generate and deliver electrical stimulation therapy other than cardioversion or defibrillation shocks, including anti-tachycardia pacing (ATP), post-shock pacing, bradycardia pacing, high rate pacing for VF induction, and/or entrainment pacing pulses before a T-shock for VF induction using a therapy vector formed from one or more any of a variety of electrode vectors that include one or more of the electrode segments 24 and/or electrodes 28A and/or 28B and/or 30, and/or the housing electrode of ICD 14. For example, ICD 14 may deliver pacing pulses via an electrode vector in which one or more of electrodes 28A, 28B, or 30, or electrode segments 24A and 24B (individually or collectively) is a cathode and the housing electrode is an anode or vice versa. In another example, ICD 14 may deliver pacing pulses via an electrode vector formed from various pairs or multiple configurations of electrodes 28A, 28B, 30, and/or electrode segments 24A and 24B (individually or collectively), e.g., one or more of the electrodes serve as a cathode and another one or more of the electrodes serve as an anode. In yet another example, ICD 14 may deliver pacing pulses via an electrode vector between any combination of electrodes 28A, 28B, 30, and/or electrode segments 24A and 24B (individually or collectively) concurrently used as a cathode (or anode) and the housing electrode of ICD 14 as an anode or vice versa, as is the case in multi-site or multi-point pacing. In a further example, ICD 14 may pace from one or more of electrodes 28A, 28B, and 30 to an individual defibrillation electrode segment (e.g., 24A or 24B) when the segments 24 are electrically coupled to separate conductors or from one or more of electrodes 28A, 28B, and 30 to the overall defibrillation electrode formed by the combination of segments 24A and 24B when segments are electrically coupled to a single conductor within lead body 16 or the segments 24 are tied/jumpered together. Such an electrode vector may limit extracardiac stimulation, improve pacing performance, allow for selection of another vector based on anatomy, or provide other benefit(s).

The examples illustrated in FIGS. 1A and 1B are exemplary in nature and should not be considered limiting of the techniques described in this disclosure. In other examples, ICD 14 and lead 16 may be implanted at other locations. For example, ICD 14 may be implanted in a subcutaneous pocket in the right pectoral region. In this example, defibrillation lead 16 may extend subcutaneously from the device toward the manubrium of sternum 22 and bend or turn and extend inferior from the manubrium to the desired location subcutaneously or substernally. In yet another example, ICD 14 may be placed abdominally or intrathoracically. Lead 16 may be implanted in other extravascular or extracardiac locations as well. For instance, as described with respect to FIGS. 2A-2C, the distal portion of lead 16 may be implanted underneath the sternum/ribcage in the substernal space.

In the example illustrated in FIG. 1, system 10 is an ICD system that provides cardioversion/defibrillation and, in some instances, pacing therapy. However, these techniques may be applicable to other cardiac systems, including cardiac resynchronization therapy defibrillator (CRT-D) systems or other cardiac stimulation therapies, or combinations thereof. For example, ICD 14 may be configured to provide electrical stimulation pulses to stimulate nerves, skeletal muscles, diaphragmatic muscles, e.g., for various neurocardiac applications and/or for sleep apnea or respiration therapy. As another example, lead 16 may be placed further superior such that at least one of the defibrillation electrode segments 24 is placed substantially over the atrium of heart 26 to provide a shock or pulse to the atrium to terminate atrial fibrillation (AF). In still other examples, defibrillation lead 16 may include a second defibrillation electrode (e.g., second elongated coil electrode) near a proximal end of lead 16 or near a middle portion of lead 16.

Figure 2A:
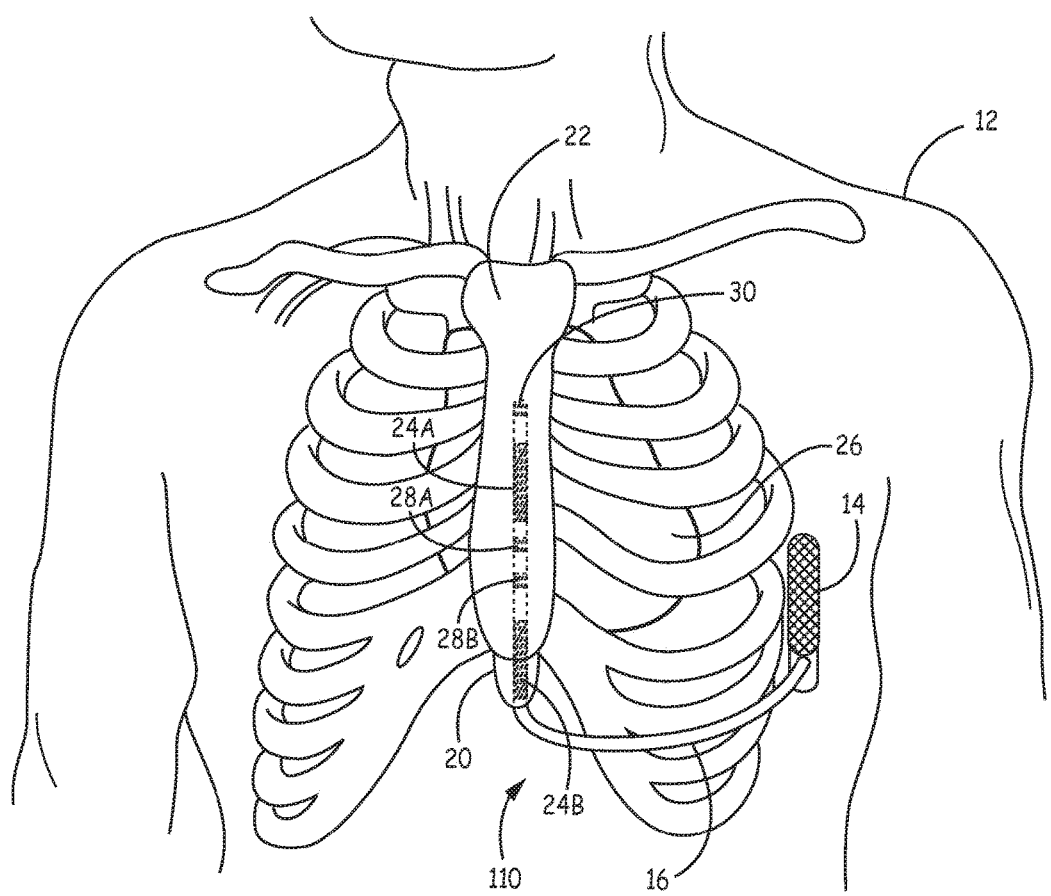
FIGS. 2A-2C are conceptual drawings illustrating various views of a patient implanted with an example extravascular ICD system in which a distal portion of the lead is implanted substernally.
Figure 2B:
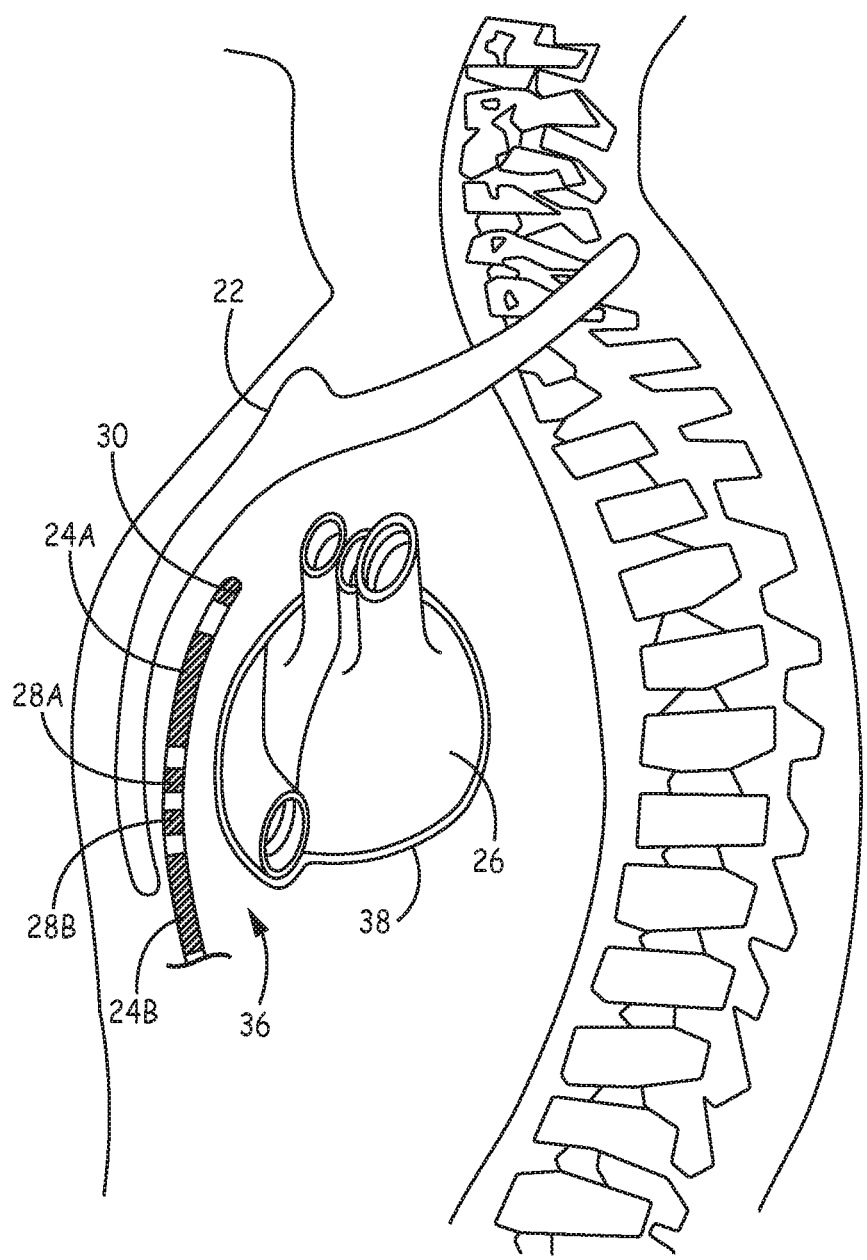
Figure 2C:
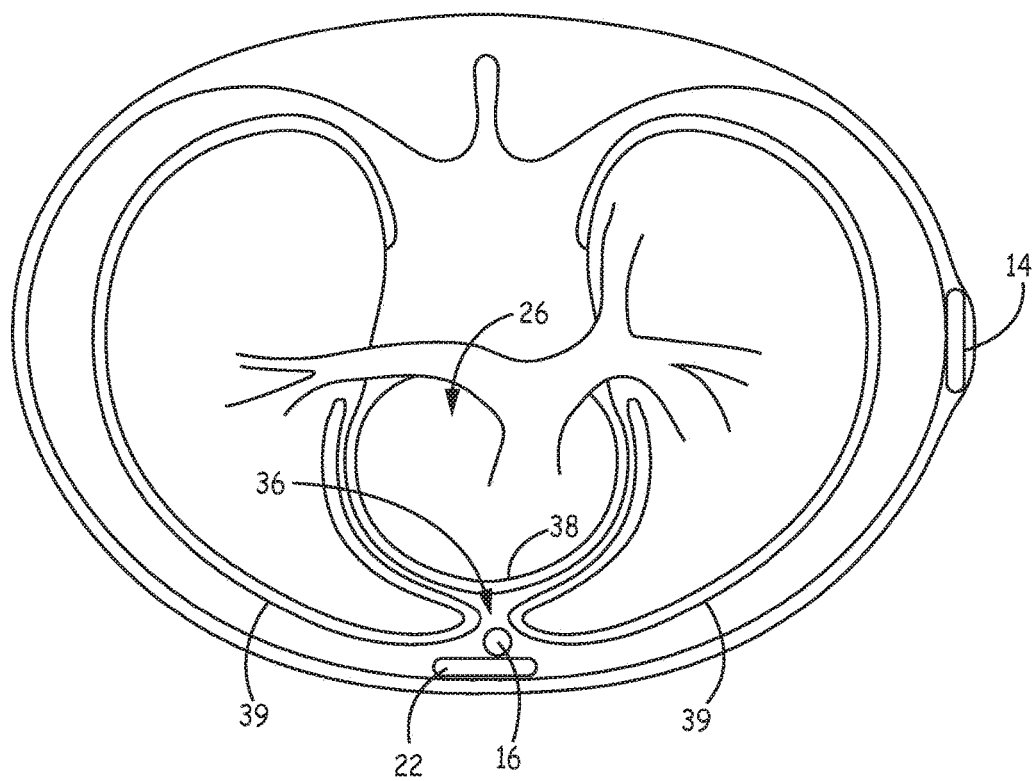

FIGS. 2A-2C are conceptual diagrams of patient 12 implanted with another example ICD system 110. FIG. 2A is a front view of patient 12 implanted with ICD system 110. FIG. 2B is a side view of patient 12 implanted with ICD system 110. FIG. 2C is a transverse view of patient 12 implanted with ICD system 110. ICD system 110 can include one or more of the structure and/or functionality of system 10 of FIGS. 1A-1B (and vice versa). ICD system 110 of FIGS. 2A-2C is illustrated with lead 16 for purposes of illustration, but may be utilized with any of lead 16 or any of the other leads described in this disclosure. Repetitive description of like numbered elements described in other embodiments is omitted for sake of brevity.

ICD system 110 conforms substantially to ICD system 10 of FIGS. 1A-1B, except defibrillation lead 16 of system 110 is implanted at least partially underneath sternum 22 of patient 12. Lead 16 extends subcutaneously from ICD 14 toward xiphoid process 20, and at a location near xiphoid process 20 bends or turns and extends superior underneath/below sternum 22 within anterior mediastinum 36. Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 16 extends along the posterior side of sternum 22 substantially within the loose connective tissue and/or substernal musculature of anterior mediastinum 36. A lead implanted such that the distal portion is substantially within anterior mediastinum 36 will be referred to herein as a substernal lead. Also, electrical stimulation, such as pacing, cardioversion or defibrillation, provided by lead 16 implanted substantially within anterior mediastinum 36 will be referred to herein as substernal electrical stimulation, substernal pacing, substernal cardioversion, or substernal defibrillation.

The distal portion of lead 16 is described herein as being implanted substantially within anterior mediastinum 36. Thus, points along the distal portion of lead 16 may extend out of anterior mediastinum 36, but the majority of the distal portion is within anterior mediastinum 36. In other embodiments, the distal portion of lead 16 may be implanted in other extracardiac, non-vascular, extra-pericardial locations, including the gap, tissue, or other anatomical features around the perimeter of and adjacent to, but not attached to, the pericardium or other portion of heart 26 and not above sternum 22 or ribcage. As such, lead 16 may be implanted anywhere within the "substernal space" defined by the undersurface between the sternum and/or ribcage and the body cavity but not including the pericardium or other portion of heart 26. The substernal space may alternatively be referred to by the terms "retrosternal space" or "mediastinum" or "infrasternal" as is known to those skilled in the art and includes the anterior mediastinum 36. The substernal space may also include the anatomical region described in Baudoin, Y. P., et al., entitled "The superior epigastric artery does not pass through Larrey's space (trigonum sternocostale)," Surg. Radiol. Anat. 25.3-4 (2003): 259-62. In other words, the distal portion of lead 16 may be implanted in the region around the outer surface of heart 26, but not attached to heart 26. Moreover, in some instances, substernal space may include inside the pleural membrane.

The distal portion of lead 16 may be implanted substantially within anterior mediastinum 36 such that electrodes 28A and 28B are located near a ventricle of heart 26. To achieve improved sensing and/or pacing, it is desirable to have the pace/sense electrodes located substantially over the chamber of heart 26 that is being paced and/or sensed. For instance, lead 16 may be implanted within anterior mediastinum 36 such that electrodes 28A and 28B are located over a cardiac silhouette of one or both ventricles as observed via an AP fluoroscopic view of heart 26. In other words, lead 16 may be implanted such that one or both of a unipolar pacing/sensing vector from electrode 28A or 28B to a housing electrode of ICD 14 are substantially across the ventricles of heart 26. In another example, the spacing between electrodes 28A and 28B as well as the placement of lead 16 may be such that a bipolar pacing vector between electrodes 28A and 28B is centered or otherwise located over the ventricle.

Likewise, to achieve improved defibrillation therapy, it is desirable to have the defibrillation electrode segments 24A and 24B located substantially over the chamber of heart 26 to which the defibrillation or cardioversion shock is being applied, e.g., over a cardiac silhouette of the ventricle as observed via an AP fluoroscopic view of heart 26. In conventional subcutaneous lead designs, it is only possible to position either the defibrillation electrode or the sense electrode over the relevant chamber, but not both. Thus, not only are electrodes 28A and 28B located over the ventricle, but due to the layout of the electrodes on the lead 16, defibrillation electrode segments 24A and 24B are also substantially located over the cardiac silhouette of the ventricle as observed via an AP fluoroscopic view of heart 26. In this manner, lead 16 is designed to provide desirable electrode positioning for both defibrillation and pacing/sensing concurrently.

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally enough such that all or a portion of lead 16 is underneath/below the ribcage in addition to or instead of sternum 22.

Placing lead 16 in the substernal space may provide a number of advantages. For example, placing lead 16 in the substernal space may significantly reduce the amount of energy that needs to be delivered to defibrillate heart 26 compared to energy required to defibrillate the heart when the electrodes of the lead are placed subcutaneously. In some instances, ICD 14 may generate and deliver cardioversion or defibrillation shocks having energies of less than 65 Joules (J), less than 60 J, between 35-60 J, and in some cases possibly less than 35 J. As such, placing defibrillation lead 16 within the substernal space, e.g., with the distal portion substantially within anterior mediastinum 36, may result in reduced energy consumption and, in turn, smaller devices and/or devices having increased longevity compared to devices used in conjunction with leads in which the electrodes are placed subcutaneously above the ribcage and/or sternum.

Another advantage of placing lead 16 in the substernal space is that pacing, such as anti-tachycardia pacing (ATP), post-shock pacing and, in some cases, bradycardia pacing, may be provided by system 110. For example, ICD 14 may deliver one or more sequences of ATP in an attempt to terminate a detected VT without delivering a defibrillation shock. The pacing (whether ATP, post-shock pacing, or bradycardia pacing) may be delivered via any of the electrode vectors described above with respect to FIGS. 1A and 1B. For example, pacing may be delivered via one or more electrode vectors of lead 16, e.g., unipolar electrode vector, bipolar electrode vector (true or integrated) or multipolar electrode vector, formed using any of the following: electrodes 28A, 28B, and 30, the housing electrode of ICD 14, and/or defibrillation electrode segments 24A and 24B collectively or individually. If the one or more sequences of ATP are not successful, it is determined that ATP is not desired (e.g., in the case of VF), or ICD 14 is not configured to deliver ATP, ICD 14 may deliver one or more cardioversion or defibrillation shocks via defibrillation electrode segments 24A or 24B of lead 16. ICD 14 may deliver the cardioversion or defibrillation shocks using either of the electrode segments 24A and 24B (or any additional electrode segments 24 not depicted) individually or together collectively. ICD 14 may generate and deliver electrical stimulation therapy other than ATP, cardioversion or defibrillation shocks, including post-shock pacing, bradycardia pacing, high rate pacing for VF induction, entrainment pacing pulses before a T-shock for VF induction and/or to sense low voltage signals and/or other electrical stimulation therapy using a therapy vector formed from one or more of electrodes 28A, 28B, 30, and/or electrode segments 24A and 24B (individually or collectively), and/or the housing electrode.

In one example, ICD 14 may deliver pacing (e.g., ATP or post-shock pacing) using an electrode vector that includes one or both defibrillation electrode segments 24A and/or 24B. The electrode vector used for pacing may, for example, include electrode segment 24A as an cathode (or anode) and one of electrode segment 24B and/or electrodes 28A, 28B, 30, or the housing of ICD as the anode (or cathode) or include segment 24B as an cathode (or anode) and one of electrode segment 24A and/or electrodes 28A, 28B, 30 or the housing of ICD as the anode (or cathode), or include segments 24A and 24B together as a common cathode (or anode) and one electrodes 28A, 28B, 30, or the housing of ICD as the anode (or cathode). If high voltage therapy is necessary, ICD 14 may deliver a cardioversion/defibrillation shock (or multiple shocks) using both of electrode segments 24A or 24B concurrently as the cathode and the housing electrode of ICD 14 as the anode.

ICD 14 may also generate and deliver electrical stimulation signals for inducing VF, e.g., high rate pacing pulses and/or entrainment pacing pulses preceding a T-shock. In one example, ICD 14 may deliver high rate pacing pulses using an electrode vector between defibrillation electrode segments 24A and 24B (e.g., one of segments 24 function as an anode and one of segments functioning as a cathode). In another example, ICD 32 may deliver a plurality of entrainment pacing pulses (e.g., 3-5 pulses) using an electrode vector between defibrillation electrode segments 24A and 24B and then deliver a shock adjacent a T-wave using defibrillation electrode segments 24A and 24B collectively as a cathode and a housing electrode of ICD 14 as an anode.

Figure 3:
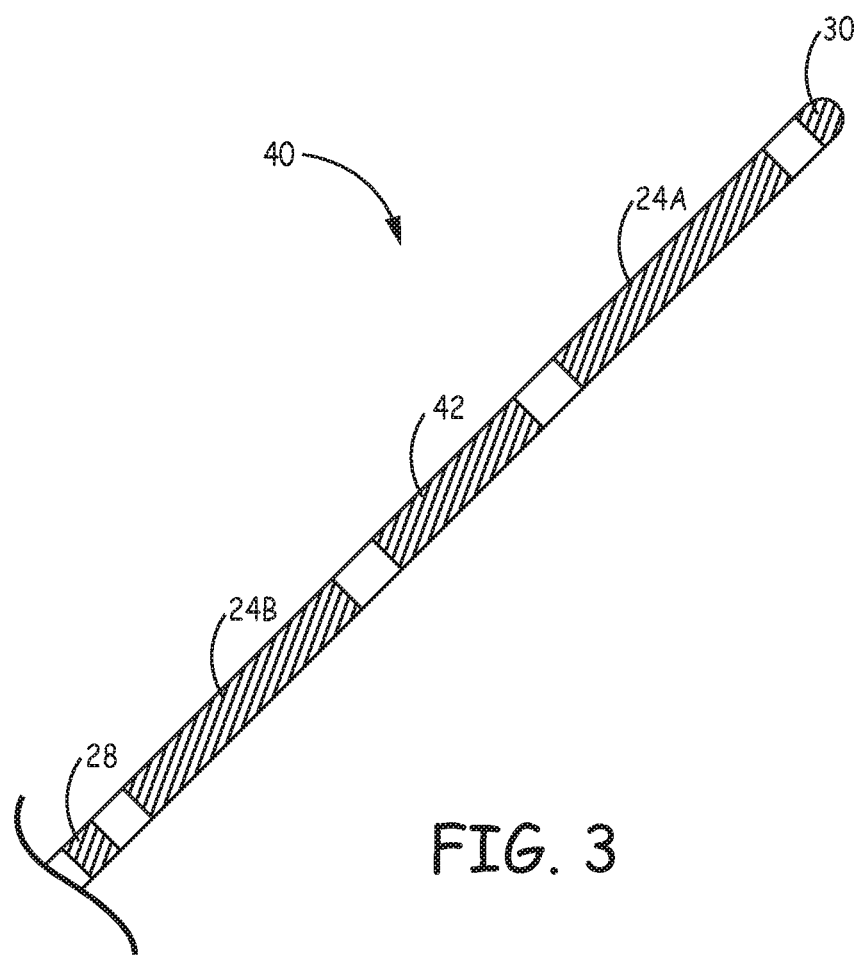
FIG. 3 is a drawing illustrating a distal portion of an example extravascular implantable medical electrical lead.

FIG. 3 is a conceptual diagram illustrating a distal portion of another example implantable electrical lead 40 with improved pacing and/or sensing capability for use in extracardiac, extravascular, non-vascular, and/or extra-pericardial applications. Lead 40 can include one or more of the structure and/or functionality of lead 16 of FIGS. 1A-1B and FIGS. 2A-2C (and vice versa). Repetitive description of like numbered elements described in other embodiments is omitted for sake of brevity. Lead 40 may be used in place of lead 16 in ICD system 10 of FIGS. 1A and 1B or ICD system 110 of FIGS. 2A-2C.

Lead 40 conforms substantially with lead 16 of FIGS. 1A and 1B, but instead of having ring electrodes 28A and 28B located between defibrillation electrode segments 24A and 24B, lead 40 includes a pace/sense coil electrode 42 between defibrillation electrode segments 24A and 24B and a pace/sense ring electrode 28 proximal to defibrillation electrode segment 24B. Such a configuration may increase the surface area of the pace/sense electrode located over the ventricle(s). However, pace/sense coil electrode 42 may be positioned elsewhere along lead body 40, including distal to defibrillation electrode segment 24A, proximal to defibrillation electrode segment 24B or between additional defibrillation electrode segments 24 not depicted. Lead 40 may thus contain more than one pace/sense coil electrode 42 along its length, and pace/sense coil electrodes 42 may be the same or different from each other in terms of size, shape, type or material. Moreover a portion of coil 42 may be partially coated or masked with a polymer (e.g., polyurethane) or another coating material (e.g., tantalum pentoxide) on one side or in different regions so as to direct the pacing signal toward heart 26 and not outward toward skeletal muscle.

Defibrillation electrode segments 24A and/or 24B may have any of the lengths (individual or total) described above with respect to FIGS. 1A and 1B and may be substantially the same length or different lengths. Additionally, defibrillation electrode segments 24A and 24B may be spaced apart from one another by any of the distances described above with respect to FIGS. 1A and 1B. Pace/sense coil electrode 42 may have a length of between approximately greater than or equal to 0.5 and less than or equal to 3 cm. Pace/sense coil electrode 42 is also spaced apart from defibrillation electrode segments 24A and 24B (e.g., the proximal end of electrode 42 is spaced apart from the distal end of electrode segment 24B and the distal end of electrode 42 is spaced apart from the proximal end of electrode segment 24A) by the distances described above with respect to FIGS. 1A and 1B. As such, the length of pace/sense coil electrode 42 may be dependent upon the spacing between defibrillation electrode segments 24A and 24B. In one example, defibrillation electrode segments 24A and 24B may each have lengths approximately equal to 4 cm and be spaced apart by a distance greater than 1 cm. In this case, the pace/sense coil electrode 42 may have a length of approximately 1 cm. However, other spacings and lengths greater than or less than 1 cm may be used, including the ranges provided above with respect to FIGS. 1A and 1B.

As described above, lead 40 of FIG. 3 includes a tip electrode 30 distal to defibrillation electrode segment 24A and a ring electrode 28 proximal to defibrillation electrode segment 24B. Tip electrode 30 may be spaced apart from defibrillation electrode segment 24A and ring electrode 28 may be spaced apart from defibrillation electrode segment 24B by any of the distances described above with respect to FIGS. 1A and 1B. In some instances, the distal portion of lead 40 from the distal end of lead 40 to the proximal side of the most proximal electrode (e.g., electrode 28 in the example of FIG. 3) may be less than or equal 15 cm and, more preferably, less than or equal to 13 cm and even more preferably less than or equal to 10 cm.

Although illustrated as a ring electrode and hemispherical electrode, respectively, electrodes 28 and 30 may comprise any of a number of different types of electrodes, including ring electrodes, short coil electrodes, paddle electrodes, hemispherical electrodes, directional electrodes, segmented electrodes, or the like, and may be positioned at any position along the distal portion of lead 40. Further, electrodes 28 and 30 may be of similar type, shape, size and material or may differ from each other.

Moreover, in other embodiments lead 40 may not include one or both of electrodes 28 and/or 30. For example, lead 40 may include coil electrode 42 as the only pace/sense electrode on lead 40 and not include either of electrodes 28 or 30. In another example, lead 40 may include distal electrode 30 and coil electrode 42 as pace/sense electrodes and not include proximal electrode 28. In a further example, lead 40 may include proximal electrode 28 and coil electrode 42 as pace/sense electrodes and not include distal electrode 30. In all of the examples in this paragraph, lead 40 includes defibrillation electrode segments 24A and 24B (and additional defibrillation electrode segments 24, not depicted), which may be used for pacing and sensing as well.

ICD 14 may be configured to sense and deliver pacing and/or cardioversion/defibrillation using any combination of electrode segments 24A and/or 24B, and/or electrodes 28, 30, 42, and/or the housing electrode. ICD may deliver electrical stimulation and/or sense using any electrode vector that includes defibrillation electrode segments 24A and 24B (individually or collectively), and/or electrodes 28, 30, and/or 42, and/or the housing electrode of ICD 14. For example, ICD 14 may deliver pacing pulses via an electrode vector in which one or more of electrodes 28, 30, 42, or electrode segments 24A and/or 24B (individually or collectively) is a cathode and the housing electrode of ICD 14 is an anode or possibly any combination or cathode and anode configurations. In another example, ICD 14 may deliver pacing pulses via an electrode vector formed from various pairs or multiple configurations of electrodes 28, 30, 42, or electrode segments 24A and/or 24B (individually or collectively), e.g., one or more of the electrodes and/or segments serves as a cathode and another one or more of the electrodes and/or segments serves as an anode. In yet another example, ICD 14 may deliver pacing pulses via an electrode vector between any combination of electrodes 28, 30, 42, and/or electrode segments 24A and/or 24B (individually or collectively) that are concurrently used as a cathode and the housing electrode of ICD 14 is used as an anode or vice versa, as is the case in multi-site or multi-point pacing.

Lead 40 may be implanted in any of the locations described above with respect to FIGS. 1A-1B and FIGS. 2A-2C, e.g., such that electrode 42 and/or defibrillation electrode segment(s) 24 are substantially over the ventricular surface of the cardiac silhouette.

Figure 4:
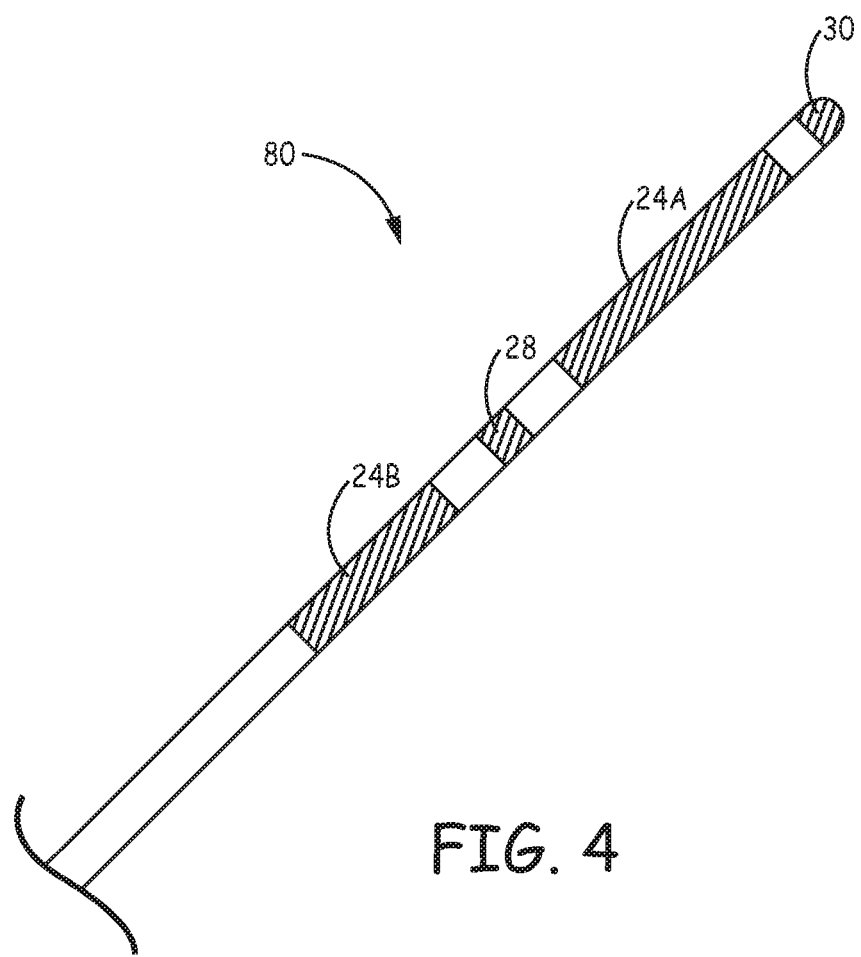
FIG. 4 is a drawing illustrating a distal portion of another example extravascular implantable medical electrical lead.

FIG. 4 is a conceptual diagram illustrating a distal portion of another example implantable electrical lead 80 with improved pacing and/or sensing capability for use in extracardiac, extravascular, non-vascular, and/or extra-pericardial applications. Lead 80 can include one or more of the structure and/or functionality of lead 16 of FIGS. 1A-1B and FIGS. 2A-2C (and vice versa) and/or lead 40 of FIG. 3 (and vice versa). Repetitive description of like numbered elements described in other embodiments is omitted for sake of brevity. Lead 80 may be used in place of lead 16 in ICD system 10 of FIGS. 1A and 1B or ICD system 110 of FIGS. 2A-2C.

Lead 80 conforms substantially with lead 16 of FIGS. 1A and 1B, but instead of having ring electrodes 28A and 28B located between defibrillation electrode segments 24A and 24B, lead 80 includes only a single pace/sense electrode 28 between defibrillation electrode segments 24A and 24B and different defibrillation electrode segment lengths.

Defibrillation electrode segments 24A and/or 24B of FIG. 4 are of different lengths. In particular, defibrillation electrode segment 24A is longer than defibrillation electrode segment 24B. In other instances, however, defibrillation electrode segment 24B may be longer than defibrillation electrode segment 24A or the two may have substantially the same length. The lengths (individual or total) of segments 24A and 24B may be the same as described above with respect to FIGS. 1A and 1B. Additionally, defibrillation electrode segments 24A and 24B may be spaced apart from one another by any of the distances described above with respect to FIGS. 1A and 1B.

Lead 80 includes a tip electrode 30 distal to defibrillation electrode segment 24A and ring electrode 28 between defibrillation electrode segment 24A and 24B. Tip electrode 30 may be spaced apart from defibrillation electrode segment 24A and ring electrode 28 may be spaced apart from defibrillation electrode segments 24A and 24B by any of the distances described above with respect to FIGS. 1A and 1B. In some instances, the distal portion of lead 80 from the distal end of lead 80 to the proximal side of the most proximal electrode (e.g., electrode segment 24B in the example of FIG. 4) may be less than or equal 15 cm and, more preferably, less than or equal to 13 cm and even more preferably less than or equal to 10 cm.

Although illustrated as a ring electrode and hemispherical electrode, respectively, electrodes 28 and 30 may comprise any of a number of different types of electrodes, including ring electrodes, short coil electrodes, paddle electrodes, hemispherical electrodes, directional electrodes, segmented electrodes, or the like, and may be positioned at any position along the distal portion of lead 80. Further, electrodes 28 and 30 may be of similar type, shape, size and material or may differ from each other.

Moreover, in other embodiments lead 80 may not include one or both of electrodes 28 and/or 30. For example, lead 80 may include electrode 28 between defibrillation segments 24A and 24B but not include electrode 30. In another example, lead 80 may include electrode 28 between defibrillation segments 24A and 24B and include another pace/sense electrode proximal to defibrillation electrode segment 24B in addition to or instead of pace/sense electrode 30. In other instances, lead 80 may include more than one pace/sense electrode distal to electrode segment 24A and/or more than one pace/sense electrode between defibrillation electrode segments 24A and 24B and/or more than one pace/sense electrode proximal to defibrillation electrode segment 24B. In all of the examples in this paragraph, lead 80 includes defibrillation electrode segments 24A and 24B, which may be used for pacing and sensing as well.

ICD 14 may be configured to sense and/or deliver pacing and/or cardioversion/defibrillation using any combination of electrode segments 24A and/or 24B, electrodes 28, 30, and the housing electrode. ICD may deliver electrical stimulation and/or sense using any electrode vector that includes defibrillation electrode segments 24A and 24B (individually or collectively), and/or electrodes 28 and/or 30, and/or the housing electrode of ICD 14. For example, ICD 14 may deliver pacing pulses via an electrode vector in which one of electrodes 28, 30, or electrode segments 24A and/or 24B (individually or collectively) is a cathode and the housing electrode of ICD 14 is an anode or vice versa. In another example, ICD 14 may deliver pacing pulses via an electrode vector formed from various pairs or multiple configurations of electrodes 28, 30, and/or electrode segments 24A and/or 24B, as well as additional electrode segments 24 not depicted, (individually or collectively), e.g., one or more of the electrodes and/or segments serves as a cathode and another one or more of the electrodes and/or segments serves as an anode. In yet another example, ICD 14 may deliver pacing pulses via an electrode vector between any combination of electrodes 28, 30, and/or electrode segments 24A and/or 24B (individually or collectively) that are concurrently used as a cathode and the housing electrode of ICD 14 is used as an anode or vice versa, as is the case in multi-site or multi-point pacing.

Lead 80 may be implanted in any of the locations described above with respect to FIGS. 1A-1B and FIGS. 2A-2C, e.g., such that electrode 28 and/or defibrillation electrode segments 24A and/or 24B are substantially over the ventricular surface of the cardiac silhouette.

Figure 5:
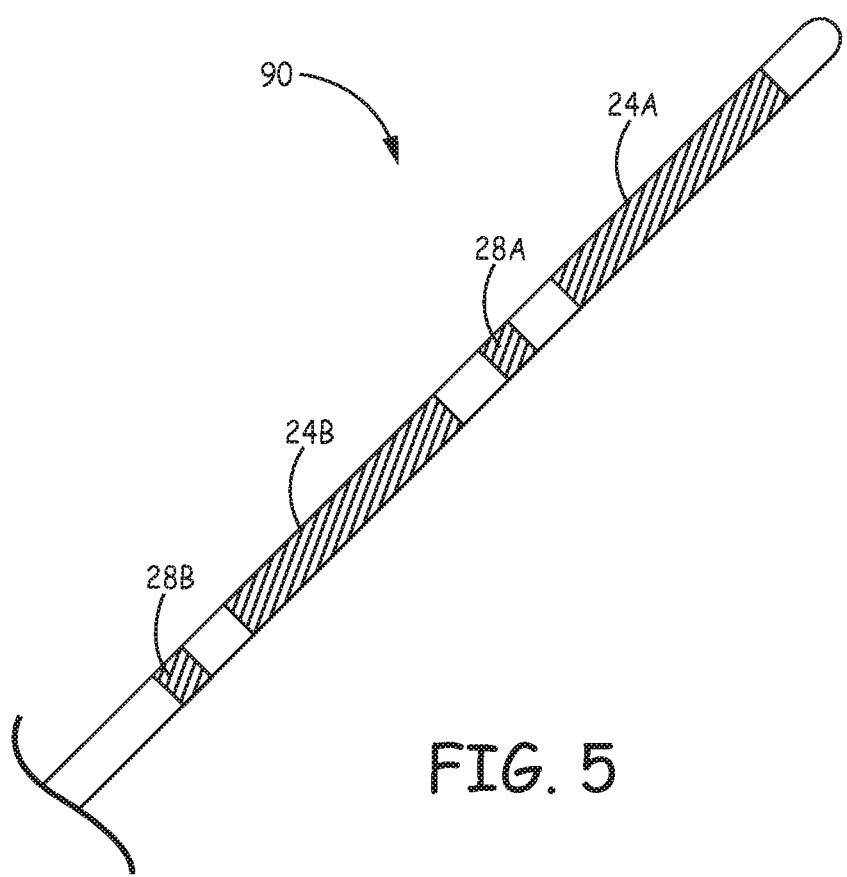
FIG. 5 is a drawing illustrating a distal portion of another example extravascular implantable medical electrical lead.

FIG. 5 is a conceptual diagram illustrating a distal portion of another example implantable electrical lead 90 with improved pacing and/or sensing capability for use in extracardiac, extravascular, non-vascular, and/or extra-pericardial applications. Lead 90 can include one or more of the structure and/or functionality of lead 16 of FIGS. 1A-1B and FIGS. 2A-2C (and vice versa), lead 40 of FIG. 3 (and vice versa), and/or lead 80 of FIG. 4 (and vice/versa). Repetitive description of like numbered elements described in other embodiments is omitted for sake of brevity. Lead 90 may be used in place of lead 16 in ICD system 10 of FIGS. 1A and 1B or ICD system 110 of FIGS. 2A-2C.

Lead 90 includes defibrillation electrode segments 24A and 24B, a first pace/sense electrode 28A disposed between defibrillation electrode segments 24A and 24B, and a second pace/sense electrode 28B disposed proximal to defibrillation electrode segment 24B. Defibrillation electrode segments 24A and/or 24B may have any of the lengths (individual or total) described above with respect to FIGS. 1-4 and may be substantially the same length or different lengths. Additionally, defibrillation electrode segments 24A and 24B may be spaced apart from one another by any of the distances described above with respect to FIGS. 1-4.

Pace/sense electrodes 28 are spaced apart from defibrillation electrode segments 24A and 24B by the distances described above with respect to FIGS. 1-4. In some instances, the distal portion of lead 90 from the distal end of lead 90 to the proximal side of the most proximal electrode (e.g., electrode 28B in the example of FIG. 5) may be less than or equal 15 cm and, more preferably, less than or equal to 13 cm and even more preferably less than or equal to 10 cm. Although illustrated as ring electrodes, electrodes 28 may comprise any of a number of different types of electrodes, including ring electrodes, short coil electrodes, paddle electrodes, hemispherical electrodes, directional electrodes, segmented electrodes, or the like, and may be positioned at any position along the distal portion of lead 90. Further, electrodes 28 may be of similar type, shape, size and material or may differ from each other.

Moreover, in other embodiments, lead 90 may not include one or both of electrodes 28A and/or 28B. For example, lead 90 may include electrode 28A between defibrillation segments 24A and 24B but not include electrode 28B. In another example, electrode 28B of lead 90 may be located distal to defibrillation electrode segment 24A. In a further example, in addition to electrodes 28A and 28B, lead 90 may include a third pace/sense electrode located distal to defibrillation electrode segment 28A.

ICD 14 may deliver electrical stimulation and/or sense electrical signals using any electrode vector that includes defibrillation electrode segments 24A and 24B (individually or collectively), and/or electrodes 28A and/or 28B, and/or the housing electrode of ICD 14. For example, ICD 14 may deliver pacing pulses via an electrode vector in which one of electrodes 28A, 28B, or electrode segments 24A and/or 24B (individually or collectively) is a cathode and the housing electrode of ICD 14 is an anode or vice versa. In another example, ICD 14 may deliver pacing pulses via an electrode vector formed from various pairs or multiple configurations of electrodes 28A, 28B, and/or electrode segments 24A and/or 24B, as well as additional electrode segments 24 not depicted, (individually or collectively), e.g., one or more of the electrodes and/or segments serves as a cathode and another one or more of the electrodes and/or segments serves as an anode. In yet another example, ICD 14 may deliver pacing pulses via an electrode vector between any combination of electrodes 28A, 28B, and/or electrode segments 24A and/or 24B (individually or collectively) that are concurrently used as a cathode and the housing electrode of ICD 14 is used as an anode or vice versa, as is the case in multi-site or multi-point pacing. Many of these vectors are described in more detail above with respect to FIGS. 1-4.

Lead 90 may be implanted in any of the locations described above with respect to FIGS. 1A-1B and FIGS. 2A-2C, e.g., such that electrode 28A and/or 28B and/or defibrillation electrode segments 24A and/or 24B are substantially over the ventricular surface of the cardiac silhouette.

Figure 6:
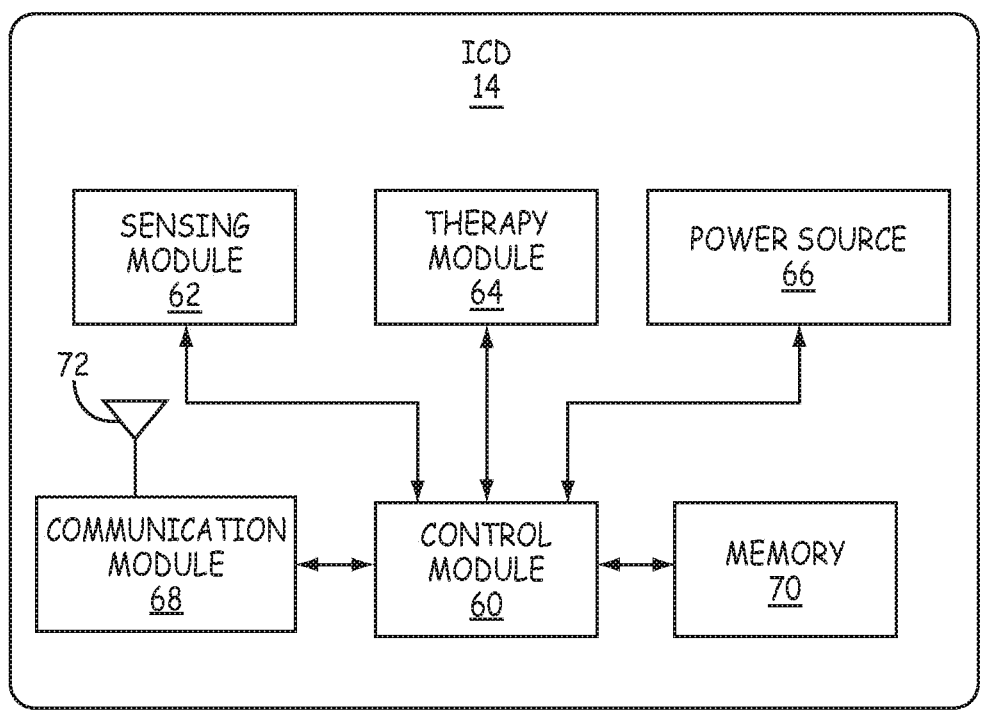
FIG. 6 is a block diagram illustrating components of an example ICD.

FIG. 6 is a functional block diagram of an example configuration of electronic components of an example ICD 14. ICD 14 includes a control module 60, sensing module 62, therapy module 64, communication module 68, and memory 70. The electronic components may receive power from a power source 66, which may be a rechargeable or non-rechargeable battery. In other embodiments, ICD 14 may include more or fewer electronic components. The described modules may be implemented together on a common hardware component or separately as discrete but interoperable hardware or software components. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components. FIG. 6 will be described in the context of ICD 14 being coupled to lead 16 for exemplary purposes only. However, ICD 14 may be coupled to other leads, such as lead 40 and/or lead 80 described herein, and thus other electrodes, such as electrodes 42.

Sensing module 62 is electrically coupled to some or all of electrodes 24 (or separately to segments 24A and/or 24B), 28A, 28B, and 30 via the conductors of lead 16 and one or more electrical feedthroughs, or to the housing electrode via conductors internal to the housing of ICD 14. Sensing module 62 is configured to obtain signals sensed via one or more combinations of electrodes 24 (or segments 24A and/or 24B), 28A, 28B, and 30 and the housing electrode of ICD 14 and process the obtained signals.

The components of sensing module 62 may be analog components, digital components or a combination thereof. Sensing module 62 may, for example, include one or more sense amplifiers, filters, rectifiers, threshold detectors, analog-to-digital converters (ADCs) or the like. Sensing module 62 may convert the sensed signals to digital form and provide the digital signals to control module 60 for processing or analysis. For example, sensing module 62 may amplify signals from the sensing electrodes and convert the amplified signals to multi-bit digital signals by an ADC. Sensing module 62 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to control module 60.

Control module 60 may process the signals from sensing module 62 to monitor electrical activity of heart 26 of patient 12. Control module 60 may store signals obtained by sensing module 62 as well as any generated EGM waveforms, marker channel data or other data derived based on the sensed signals in memory 70. Control module 60 may analyze the EGM waveforms and/or marker channel data to detect cardiac events (e.g., tachycardia). In response to detecting the cardiac event, control module 60 may control therapy module 64 to deliver the desired therapy to treat the cardiac event, e.g., defibrillation shock, cardioversion shock, ATP, post-shock pacing, or bradycardia pacing.

Therapy module 64 is configured to generate and deliver electrical stimulation therapy to heart 26. Therapy module 64 may include one or more pulse generators, capacitors, and/or other components capable of generating and/or storing energy to deliver as pacing therapy, defibrillation therapy, cardioversion therapy, cardiac resynchronization therapy, other therapy or a combination of therapies. In some instances, therapy module 64 may include a first set of components configured to provide pacing therapy and a second set of components configured to provide defibrillation therapy. In other instances, therapy module 64 may utilize the same set of components to provide both pacing and defibrillation therapy. In still other instances, therapy module 64 may share some of the defibrillation and pacing therapy components while using other components solely for defibrillation or pacing.

Control module 60 may control therapy module 64 to deliver the generated therapy to heart 26 via one or more combinations of electrodes 24 (or separately to segments 24A and/or 24B), 28A, 28B, and 30 of lead 16 and the housing electrode of ICD 14 according to one or more therapy programs, which may be stored in memory 70. In instances in which control module 60 is coupled to a different lead, e.g., lead 40, 80, or 90, other electrodes may be utilized, such as electrodes 28 and 42. Control module 60 controls therapy module 64 to generate electrical stimulation therapy with the amplitudes, pulse widths, timing, frequencies, electrode combinations or electrode configurations specified by a selected therapy program.

Therapy module 64 may include a switch module to select which of the available electrodes are used to deliver the therapy. The switch module may include a switch array, switch matrix, multiplexer, or any other type of switching device suitable to selectively couple electrodes to therapy module 64. Control module 60 may select the electrodes to function as therapy electrodes, or the therapy vector, via the switch module within therapy module 64. In instances in which defibrillation segments 24A and 24B are each coupled to separate conductors, control module 60 may be configured to selectively couple therapy module 64 to either one of segments 24A or 24B individually or couple to both of the segments 24A and 24B concurrently. In some instances, the same switch module may be used by both therapy module 64 and sensing module 62. In other instances, each of sensing module 62 and therapy module 64 may have separate switch modules.

In the case of pacing therapy being provided, e.g., ATP, post-shock pacing, and/or bradycardia pacing provided via electrodes 28A, 28B, 30, and/or defibrillation electrode segments 24A or 24B of lead 16. In one example, therapy module 64 may deliver pacing (e.g., ATP or post-shock pacing) using an electrode vector that includes one or both defibrillation electrode segments 24A and/or 24B. The electrode vector used for pacing may be segment 24A as an anode (or cathode) and one of electrodes 24B, 28A, 28B, 30 or the housing of ICD as the cathode (or anode) or segment 24B as an anode (or cathode) and one of electrodes 24A, 28A, 28B, 30 or the housing of ICD as the cathode (or anode). If necessary, therapy module 64 may generate and deliver a cardioversion/defibrillation shock (or shocks) using one or both of electrode segments 24A or 24B concurrently as a cathode and the housing electrode of ICD 14 as an anode.

Control module 60 controls therapy module 64 to generate and deliver pacing pulses with any of a number of shapes, amplitudes, pulse widths, or other characteristic to capture heart 26. For example, the pacing pulses may be monophasic, biphasic, or multiphasic (e.g., more than two phases). The pacing thresholds of heart 26 when delivering pacing pulses from the substernal space, e.g., from electrodes 28A, 28B, and/or 30 and/or electrode segments 24 substantially within anterior mediastinum 36, may depend upon a number of factors, including location, type, size, orientation, and/or spacing of electrodes 28A, 28B, and 30 and/or electrode segments 24, location of ICD 14 relative to electrodes 28A, 28B, and 30 and/or electrode segments 24, physical abnormalities of heart 26 (e.g., pericardial adhesions or myocardial infarctions), or other factor(s).

The increased distance from electrodes 28A, 28B, and 30 and/or electrode segments 24 of lead 16 to the heart tissue may result in heart 26 having increased pacing thresholds compared to transvenous pacing thresholds. To this end, therapy module 64 may be configured to generate and deliver pacing pulses having larger amplitudes and/or pulse widths than conventionally required to obtain capture via leads implanted within the heart (e.g., transvenous leads) or leads attached directly to heart 26. In one example, therapy module 64 may generate and deliver pacing pulses having amplitudes of less than or equal to 8 volts and pulse widths between 0.5-3.0 milliseconds and, in some instances up to 4 milliseconds. In another example, therapy module 64 may generate and deliver pacing pulses having amplitudes of between 5 and 10 volts and pulse widths between approximately 3.0 milliseconds and 10.0 milliseconds. In another example, therapy module 64 may generate and deliver pacing pulses having pulse widths between approximately 2.0 milliseconds and 8.0 milliseconds. In a further example, therapy module 64 may generate and deliver pacing pulses having pulse widths between approximately 0.5 milliseconds and 20.0 milliseconds. In another example, therapy module 64 may generate and deliver pacing pulses having pulse widths between approximately 1.5 milliseconds and 20.0 milliseconds.

Pacing pulses having longer pulse durations than conventional transvenous pacing pulses may result in lower energy consumption. As such, therapy module 64 may be configured to generate and deliver pacing pulses having pulse widths or durations of greater than two (2) milliseconds. In another example, therapy module 64 may be configured to generate and deliver pacing pulses having pulse widths or durations of between greater than two (2) milliseconds and less than or equal to three (3) milliseconds. In another example, therapy module 64 may be configured to generate and deliver pacing pulses having pulse widths or durations of greater than or equal to three (3) milliseconds. In another example, therapy module 64 may be configured to generate and deliver pacing pulses having pulse widths or durations of greater than or equal to four (4) milliseconds. In another example, therapy module 64 may be configured to generate and deliver pacing pulses having pulse widths or durations of greater than or equal to five (5) milliseconds. In another example, therapy module 64 may be configured to generate and deliver pacing pulses having pulse widths or durations of greater than or equal to ten (10) milliseconds. In a further example, therapy module 64 may be configured to generate and deliver pacing pulses having pulse widths between approximately 3-10 milliseconds. In a further example, therapy module 64 may be configured to generate and deliver pacing pulses having pulse widths between approximately 4-10 milliseconds. In a further example, therapy module 64 may be configured to generate and deliver pacing pulses having pulse widths or durations of greater than or equal to fifteen (15) milliseconds. In yet another example, therapy module 64 may be configured to generate and deliver pacing pulses having pulse widths or durations of greater than or equal to twenty (20) milliseconds.

Depending on the pulse widths, ICD 14 may be configured to deliver pacing pulses having pulse amplitudes less than or equal to twenty (20) volts, deliver pacing pulses having pulse amplitudes less than or equal to ten (10) volts, deliver pacing pulses having pulse amplitudes less than or equal to five (5) volts, deliver pacing pulses having pulse amplitudes less than or equal to two and one-half (2.5) volts, deliver pacing pulses having pulse amplitudes less than or equal to one (1) volt. In other examples, the pacing pulse amplitudes may be greater than 20 volts. Typically the lower amplitudes require longer pacing widths as illustrated in the experimental results. Reducing the amplitude of pacing pulses delivered by ICD 14 reduces the likelihood of extra-cardiac stimulation and lower consumed energy of power source 66.

For pacing therapy provided from the subcutaneous placement of lead 16 above the sternum and/or ribcage, pacing amplitudes and pulse widths may vary.

In the case of cardioversion or defibrillation therapy, e.g., cardioversion or defibrillation shocks provided by defibrillation electrode segments 24A and/or 24B (individually or together), control module 60 controls therapy module 64 to generate cardioversion or defibrillation shocks having any of a number of waveform properties, including leading-edge voltage, tilt, delivered energy, pulse phases, and the like. Therapy module 64 may, for instance, generate monophasic, biphasic or multiphasic waveforms. Additionally, therapy module 64 may generate cardioversion or defibrillation waveforms having different amounts of energy. As with pacing, delivering cardioversion or defibrillation shocks from the substernal space, e.g., from electrode segment(s) 24 substantially within anterior mediastinum 36, may reduce the amount of energy that needs to be delivered to defibrillate heart 26. When lead 16 is implanted in the substernal space, therapy module 64 may generate and deliver cardioversion or defibrillation shocks having energies of less than 65 J, less than 60 J, between 40-50 J, between 35-60 J, and in some instances less than 35 J. When lead 16 is implanted subcutaneously, ICD 14 may generate and deliver cardioversion or defibrillation shocks having energies around 65-80 J.

Therapy module 64 may also generate defibrillation waveforms having different tilts. In the case of a biphasic defibrillation waveform, therapy module 64 may use a 65/65 tilt, a 50/50 tilt, or other combinations of tilt. The tilts on each phase of the biphasic or multiphasic waveforms may be the same in some instances, e.g., 65/65 tilt. However, in other instances, the tilts on each phase of the biphasic or multiphasic waveforms may be different, e.g., 65 tilt on the first phase and 55 tilt on the second phase. The example delivered energies, leading-edge voltages, phases, tilts, and the like are provided for example purposes only and should not be considered as limiting of the types of waveform properties that may be utilized to provide substernal defibrillation via defibrillation electrode segment(s) 24.

Communication module 68 includes any suitable hardware, firmware, software or any combination thereof for communicating with another device, such as a clinician programmer, a patient monitoring device, or the like. For example, communication module 68 may include appropriate modulation, demodulation, frequency conversion, filtering, and amplifier components for transmission and reception of data with the aid of antenna 72. Antenna 72 may be located within connector block of ICD 14 or within housing ICD 14.

The various modules of ICD 14 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 70 may include computer-readable instructions that, when executed by control module 60 or other component of ICD 14, cause one or more components of ICD 14 to perform various functions attributed to those components in this disclosure. Memory 70 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Various examples have been described. These and other examples are within the scope of the following claims.

The invention claimed is:

1. An implantable medical electrical lead comprising:
an elongated lead body having a distal portion and a proximal end;
at least one pace/sense electrode located along the distal portion of the elongated lead body;
a defibrillation electrode located along the distal portion of the elongated lead body, wherein the defibrillation electrode includes a first defibrillation electrode segment and a second defibrillation electrode segment spaced proximal to the first defibrillation electrode segment, and wherein the distal portion of the elongated lead body is arranged such that, when the implantable medical electrical lead is implanted in a substernal location in a patient, the defibrillation electrode is substantially over a surface of a cardiac silhouette of a heart of the patient as observed via an anterior-posterior (AP) fluoroscopic view of the heart, and the at least one pace/sense electrode is over a surface of a silhouette of a ventricle of the heart as observed via the AP fluoroscopic view of the heart.

2. The implantable medical electrical lead of claim 1, wherein when the implantable medical electrical lead is implanted in the substernal location, the defibrillation electrode is substantially over a center of the surface of the silhouette of the ventricle as observed via the AP fluoroscopic view of the heart.

3. The implantable medical electrical lead of claim 1, wherein the first and second defibrillation electrode segments are spaced apart from each other by a distance of approximately 0.5 centimeters to 2 centimeters.

4. The implantable medical electrical lead of claim 3, wherein the first and second defibrillation electrode segments are spaced apart from each other by a distance of approximately 20 millimeters.

5. The implantable medical electrical lead of claim 1, wherein the at least one pace/sense electrode is located between the first and second defibrillation electrode segments.

6. The implantable medical electrical lead of claim 1, wherein the at least one pace/sense electrode is located distal to the first defibrillation electrode segment.

7. The implantable medical electrical lead of claim 1, wherein the at least one pace/sense electrode is located proximal to the second defibrillation electrode segment.

8. The implantable medical electrical lead of claim 1, wherein the at least one pace/sense electrode comprises at least two pace/sense electrodes, and wherein a first of the at least two pace/sense electrodes is located between the first and second defibrillation electrode segments and a second of the at least two pace/sense electrodes is located proximal to the second defibrillation electrode segment.

9. The implantable medical electrical lead of claim 1, wherein the at least one pace/sense electrode comprises at least two pace/sense electrodes, and wherein a first of the at least two pace/sense electrodes is located between the first and second defibrillation electrode segments and a second of the at least two pace/sense electrodes is located distal to the first defibrillation electrode segment.

10. The implantable medical electrical lead of claim 9, wherein, when the implantable medical electrical lead is implanted in the substernal location in the patient, the second of the at least two pace/sense electrodes is located over a cardiac silhouette of an atrium of the heart as observed via the AP fluoroscopic view.

11. The implantable medical electrical lead of claim 1, wherein the at least one pace/sense electrode and at least one of the first and second defibrillation electrode segments are both substantially over the surface of the silhouette of the ventricle as observed via the AP fluoroscopic view.

12. The implantable medical electrical lead of claim 11, wherein the second defibrillation electrode segment is substantially over the surface of the silhouette of the ventricle as observed via the AP fluoroscopic view.

13. The implantable medical electrical lead of claim 12, wherein the at least one pace/sense electrode and the second defibrillation electrode segment are both substantially over a center of a ventricle.

14. The implantable medical electrical lead of claim 1, wherein the substernal location comprises a location substantially within an anterior mediastinum of the patient, and wherein the distal portion of the elongated lead body is configured to be positioned in the location substantially within the anterior mediastinum of the patient.

15. An extravascular implantable cardioverter-defibrillator system comprising:
an implantable cardioverter-defibrillator (ICD) that includes a housing electrode and a therapy module configured to generate and deliver electrical stimulation therapy; and
an extravascular implantable medical electrical lead electrically coupled to the therapy module, wherein the lead comprises:
an elongated lead body having a distal portion and a proximal end;
a defibrillation electrode located along the distal portion of the elongated lead body, wherein the defibrillation electrode includes a first defibrillation electrode segment and a second defibrillation electrode segment spaced proximal to the first defibrillation electrode segment; and
at least one pace/sense electrode located along the distal portion of the elongated lead body,
wherein the distal portion of the elongated lead body is arranged such that, when the implantable medical electrical lead is implanted in a substernal location in a patient, the defibrillation electrode is substantially over a surface of a cardiac silhouette of a heart of the patient as observed via the AP fluoroscopic view and the at least one pace/sense electrode is over a surface of a silhouette of a ventricle of the heart as observed via the AP fluoroscopic view.

16. The system of claim 15, wherein the at least one pace/sense electrode comprises at least two pace/sense electrodes.

17. The system of claim 16, wherein when the implantable medical electrical lead is implanted, the at least two pace/sense electrodes are substantially located over the surface of the silhouette of the ventricle as observed via the AP fluoroscopic view.

18. The system of claim 15, wherein when the implantable medical electrical lead is implanted, a unipolar pacing vector from the at least one pace/sense electrode to the housing electrode is substantially across the ventricle.

19. The system of claim 16, wherein when the implantable medical electrical lead is implanted, the at least two pace/sense electrodes are substantially located over the surface of the silhouette of the ventricle as observed via the AP fluoroscopic view, and wherein a bipolar pacing vector between two of the at least two pace/sense electrodes is substantially over the ventricle.

20. The system of claim 15, further comprising an electrical conductor extending from the proximal end of the elongated lead body and electrically coupling to the first defibrillation electrode segment and the second defibrillation electrode segment, and wherein the first and second defibrillation electrode segments form one of a common cathode and a common anode of an electrode vector for delivery of electrical stimulation therapy.

21. The system of claim 15, further comprising:
a first electrical conductor extending from the proximal end of the elongated lead body and electrically coupling to the first defibrillation electrode segment; and
a second electrical conductor extending from the proximal end of the elongated lead body and electrically coupling to the second defibrillation electrode segment.

22. The system of claim 15, wherein a length from a distal end of the lead to a proximal side of the most proximal electrode is less than or equal 15 cm.

23. The system of claim 15, wherein the first and second defibrillation electrode segments are spaced apart from each other by a distance of approximately 20 millimeters.

24. The system of claim 15, wherein the at least one pace/sense electrode is located between the first and second defibrillation electrode segments.

25. The system of claim 15, wherein the at least one pace/sense electrode is located proximal to the second defibrillation electrode segment.

26. The system of claim 15, wherein the at least one pace/sense electrode and the second defibrillation electrode segment are both substantially over the surface of the silhouette of the ventricle of the heart as observed via the AP fluoroscopic view.

27. The system of claim 15, wherein the substernal location comprises a location substantially within an anterior mediastinum of the patient, and wherein the distal portion of the elongated lead body is configured to be positioned in the location substantially within the anterior mediastinum of the patient.

28. The system of claim 15, wherein the at least one pace/sense electrode of the lead comprises at least two pace/sense electrodes, and wherein a first of the at least two pace/sense electrodes is located between the first and second defibrillation electrode segments and a second of at least two pace/sense electrodes is located distal to the first defibrillation electrode segment.

29. The system of claim 28, wherein, when the implantable medical electrical lead is implanted in the substernal location in the patient, the second of the at least two pace/sense electrodes is located over a cardiac silhouette of an atrium of the heart as observed via the AP fluoroscopic view.

* * * * *